US010435483B2

(12) United States Patent
D'Este et al.

(10) Patent No.: US 10,435,483 B2
(45) Date of Patent: Oct. 8, 2019

(54) MEDICINES FOR TOPIC USE BASED ON SULFATED HYALURONIC ACID AS ACTIVATING OR INHIBITING AGENT OF THE CYTOKINE ACTIVITY

(71) Applicant: Fidia Farmaceutici S.p.A., Abano Terme (IT)

(72) Inventors: Matteo D'Este, Abano Terme (IT); Giovanni Gennari, Abano Terme (IT)

(73) Assignee: FIDIA FARMACEUTICI S.P.A., Abano Terme (IT)

(*) Notice: Subject to any disclaimer, the term of this patent is extended or adjusted under 35 U.S.C. 154(b) by 129 days.

(21) Appl. No.: 15/336,498

(22) Filed: Oct. 27, 2016

(65) Prior Publication Data
US 2017/0107303 A1 Apr. 20, 2017

Related U.S. Application Data

(63) Continuation of application No. 13/320,000, filed as application No. PCT/EP2010/003050 on May 14, 2010, now Pat. No. 9,504,708.

(30) Foreign Application Priority Data
May 14, 2009 (IT) .............. PD2009A0134

(51) Int. Cl.
C08B 37/00 (2006.01)
A61K 31/136 (2006.01)
A61K 31/737 (2006.01)
A61K 45/06 (2006.01)
A61K 8/73 (2006.01)
A61K 9/00 (2006.01)
A61K 38/47 (2006.01)
A61Q 1/06 (2006.01)
A61Q 11/00 (2006.01)

(52) U.S. Cl.
CPC .............. C08B 37/00 (2013.01); A61K 8/735 (2013.01); A61K 9/007 (2013.01); A61K 9/0014 (2013.01); A61K 31/136 (2013.01); A61K 31/737 (2013.01); A61K 38/47 (2013.01); A61K 45/06 (2013.01); A61Q 1/06 (2013.01); A61Q 11/00 (2013.01); C12Y 302/01035 (2013.01)

(58) Field of Classification Search
CPC ...... A61K 31/136; A61K 8/735; A61K 45/06; A61K 31/737; A61K 9/0014; A61K 9/007; A61K 38/47; A61K 31/13; A61K 2300/00; C08B 37/00; A61Q 11/00; A61Q 1/06; C12Y 302/01035
See application file for complete search history.

(56) References Cited

U.S. PATENT DOCUMENTS

| | | | |
|---|---|---|---|
| 4,303,676 | A | 12/1981 | Balazs |
| 5,639,738 | A | 6/1997 | Falk et al. |
| 5,872,109 | A | 2/1999 | Akima et al. |
| 6,027,741 | A | 2/2000 | Cialdi et al. |
| 2003/0162732 | A1 | 8/2003 | Weidner |
| 2008/0188441 | A1 | 8/2008 | Reinmuller et al. |

FOREIGN PATENT DOCUMENTS

| | | |
|---|---|---|
| EP | 0889055 A1 | 1/1999 |
| EP | 0940410 A1 | 9/1999 |
| JP | 11-279042 A | 10/1999 |
| JP | 2000178196 A | 6/2000 |
| JP | 2001163789 A | 6/2001 |
| WO | WO 95/25751 A1 | 9/1995 |
| WO | WO-9845335 A1 | 10/1998 |
| WO | WO-0174781 A1 | 10/2001 |
| WO | WO-2004004744 A1 | 1/2004 |

OTHER PUBLICATIONS

Alexis, A. F. et al., "Off-Label Dermatologic Uses of Anti-TNF-a Therapies", Journal of Cutaneous Medicine and Surgery, vol. 9, No. 6 (Dec. 2005).
Brown et al. (2005). Hyaluronic acid: A unique topical vehicle for the localized delivery of drugs to the skin, J Eur Acad Dermatol Venereol., v19(3), p. 308-318.
Chang, N-S et al., "Synthetic polysulfated hyaluronic acid is a potent inhibitor for tumor necrosis factor production", Journal of Leukocyte Biology, vol. 55, No. 6 (Jun. 1, 1994).

(Continued)

Primary Examiner — Sean C. Barron
(74) Attorney, Agent, or Firm — Birch, Stewart, Kolasch & Birch, LLP

(57) ABSTRACT

The object of the present invention relates to the new and surprising use of sulfated hyaluronic acid (HAS) as regulator agent of the cytokine activity (pro- and anti-inflammatory) and consequently the use of HAS for the preparation of a new medicine for topic use in the prevention and treatment of pathologies associated with the activation and/or deficiency of cytokines of a pro- and anti-inflammatory nature. The Applicant has in fact discovered the exclusive capacity of HAS in modulating the activity of these particular proteins, it has studied the action mechanism and demonstrated the substantial difference between the different sulfated types known in the state of the art, but above all it has demonstrated an unexpectedly high activity of HAS vs different types and strains of Herpes virus, Cytomegalovirus and the virus of vesicular stomatitis. Finally, a further object of the present invention is the use of HAS as a skin absorption promoter of drugs of an anti-inflammatory nature.

9 Claims, 8 Drawing Sheets

(56) References Cited

OTHER PUBLICATIONS

DeRuiter (2002). Non-Steroidal Antiinflammatory Drugs (NSAIDS), 26 pages.
Girish KS et al. (2007). The magic glue hyaluronan and its eraser hyaluronidase: A biological overview. Life Sciences, v80, p. 1921-1943.
Karande P. et al. (2004). Discovery of transdermal penetration enhancers by high-throughput screening. Nature Biotechnology, v22(2), p. 192-197.
Raszka WV Jr. et al. (1990). The use of hyaluronidase in the treatment of intravenous extravenous injuries. Journal of Perinatology, v1092), p. 146-149 —Abstract.

Fig. 10

| Product tested | Minim. cytotoxic conc. (µg/ml) | Minimum inhibitory concentration IC 50 (µg/ml) | | | | | | |
|---|---|---|---|---|---|---|---|---|
| | | Herpes simplex virus-1 (KOS) | Herpes simplex virus-1 (F) | Herpes simplex virus-1 (McIntyre) | Herpes simplex virus-2 (G) | Herpes simplex virus-2 (196) | Herpes simplex virus-2 (Lyons) | Vesicular stomatitis virus |
| HA-NS1 | >400 | >400 | >400 | >400 | >400 | >400 | >400 | >400 |
| HAS1 | >400 | 48 | 16 | 9,6 | 9,6 | 3,2 | 3,2 | 1,92 |
| HAS3 | >400 | 16 | 3,2 | 1,92 | 1,92 | 1,92 | 1,92 | 0,128 |
| | | | | | | | | |
| DS | >400 | 9,6 | 9,6 | 9,6 | 3,2 | 3,2 | 1,92 | 16 |
| Acyclovir | >400 | 0,384 | 0,384 | 0,64 | 0,384 | 0,384 | 0,384 | >80 |

Fig. 11

| Product tested | Minimum inhibitory concentration IC 50 (µg/ml) | |
|---|---|---|
| | Cytomegalovirus AD-169 strain | Cytomegalovirus AD Davis strain |
| HA-NS1 | >50 | >50 |
| HAS1 | 5 | 3,4 |
| HAS3 | 0,2 | 0,2 |
| | | |
| DS | 2,7 | 0,5 |

MEDICINES FOR TOPIC USE BASED ON SULFATED HYALURONIC ACID AS ACTIVATING OR INHIBITING AGENT OF THE CYTOKINE ACTIVITY

This application is a continuation of co-pending U.S. patent application Ser. No. 13/320,000 filed on Jan. 27, 2012, which is the national phase of PCT International Application No. PCT/EP2010/003050 filed on May 14, 2010, which claims the benefit of Italian Patent Application No. PD2009A000134 filed on May 14, 2009. The entire contents of all of the above applications are hereby incorporated by reference.

FIELD OF THE INVENTION

For many years now, scientific/patent literature has been studying and describing sulfated hyaluronic acid which is obtained starting from hyaluronic acid (HA) suitably sulfated according to what is described in the state of the art (EP0940410B1 and EP0702699B1), to which anticoagulant effects are attributed. HAS can also be obtained by the de-acetylation and subsequent sulfation of glucosamine of HA (defined as HA-NS) (EP0971961B1), for the production of surgical articles and pharmaceutical compositions. Patents EP0754460B1 and EP1385492B1 are also known, in which the use of HAS is described in pathologies such as, for example, ARDS (serious respiratory insufficiency), articular rheumatism and rheumatoid arthritis. An object of the present invention relates to the new and surprising cutaneous use of HAS as regulator agent of the cytokine activity, as the Applicant has discovered the exclusive capacity of HAS of modulating the activity of particular cytokines (both pro- and anti-inflammatory), it has studied its action mechanism and revealed the substantial difference between the two types of sulfated product (HAS and HA-NS), but above all the Applicant has surprisingly found an unexpectedly high activity vs different types and strains of Herpes virus, Cytomegalovirus and the virus of vesicular stomatitis.

Finally, a further object of the present invention relates to the use of HAS as a skin absorption promoter of drugs of an anti-inflammatory and hormonal nature.

Since 1970, scientists have understood that selected populations of lymphoid cells can produce and release into the circulatory bed, molecules of a protein nature not assimilable to antibodies, defined with the term "cytokines". They represent a new type of "hormone", capable of acting on different cell targets in numerous regions of the body.

The progression of scientific knowledge relating to the synthesis and biological/biochemical functions of these proteins, has altered the "old" vision of the immune system (I.S.) of the same scientific world and has opened up new horizons in understanding its numerous functions, thus creating new prospects for the treatment of different pathologies, topic and/or systemic, also comprising new therapeutic possibilities relating to the immunotherapy of cancer.

The central cell of the I.S., is the lymphocyte, it represents about 20% of all the white corpuscles and, on the basis of its various functions, forms 3 groups: lymphocyte B, lymphocyte T and killer lymphocyte. Many cytokines are soluble proteins produced by lymphocytes and/or monocytes, capable of acting against other cells/tissues also situated very far from their production site. They have immunological functions, in fact, and also regulation functions in the synthesis of other cytokines on the part of different cells of the I.S. or target cells involved in the cascade of reactions initiated by the I.S.

Numerous different cytokines have been studied so far, also having numerous different acronyms, but those studied in particular by the Applicant are: Interleukin 1 and 2, Interleukin 6, 7 and 12, hereafter defined as IL-1, IL-2, IL-6, IL-7 and IL-12 which, with TNF, are defined as cytokines of an inflammatory nature, whereas Interleukin 10 (IL-10) on the contrary, is a cytokine with strong anti-inflammatory properties.

The first cytokine to be studied was definitely IL-1: present in two forms α and β, it is a powerful inducer of pro-inflammatory processes (systemic and/or cutaneous). It is mainly produced by lymphocytes B, T and macrophages after bacterial stimulus or stimulation on the part of other agents including other cytokines; it is also secreted from peripheral neutrophils, endothelial, epithelial and smooth muscle cells, fibroblasts, Langerhans cells of the skin, osteoclasts, synoviocytes and many other types of cell. Both forms bind the same receptor and have very similar, if not identical, biological activities. Many of their pro-inflammatory functions are linked to the stimulation of other cytokines, such as IL-6 and IL-8, and their very synthesis can be induced by cytokines such as TNF, Interferon, bacterial endotoxins, viruses and different types of other antigens. It is involved in septic shock but it should also be noted that recent studies have demonstrated that IL-1 is capable of activating the expression of some oncogenes and consequently of participating in the pathogenesis of neoplasias. Combined with other cytokines, IL-1 therefore represents one of the major mediators of inflammatory processes: it stimulates T-cells in fact to produce IL-2 and B-cells to produce immunoglobulins. It is also involved in the pathogenesis of rheumatoid arthritis and arthrosis: high quantities of IL-1 have in fact been found in the synovial fluid of patients affected by rheumatoid arthritis and/or osteoarthrosis. It is also active in numerous pathologies of a prevalently cutaneous nature, such as dermatitis in general, atopic dermatitis and psoriasis. Finally, it participates in the establishment of vascular damage such as venous thrombosis and is present in all vessels with pathologies of the arterio/arterioschlerotic type. Receptor antagonists are currently already in clinical use (and also being experimented) for this cytokine, as blockage of the receptor is proving to be an effective way of treating these pathologies in which IL-1 is among the protagonists.

TNF:

The necrosis factor is part of the group of cytokines which promotes the acute systemic inflammation phase. TNF is therefore involved in an extremely wide number of processes such as cell proliferation, differentiation and apoptosis, carcinogenesis and viral replication.

It is mostly produced by macrophages and by a series of other cell types including mastocytes, lymphoid cells, muscular and endothelial cells, fibroblasts and nerve cells. Its synthesis can be stimulated by bacterial endotoxins, other cytokines such as IL-2, Interferon and IL-1, and it can be inhibited by steroids.

By acting on numerous organs and systems, generally together with other cytokines, it participates in the establishment and regulation of many pathogenetic processes:
  it modulates the expression of many proteins and important cytokines, such as IL-1 and IL-6, thus resulting involved in cutaneous pathologies such as vitiligo, eczema, psoriasis and dermatitis in general;
  it stimulates the synthesis of collagenasis in the synoviocytes and for this reason, large quantities of TNF have been found in the synovial fluids of patients suffering from arthrosis and rheumatoid arthritis;

it activates the osteoclasts and therefore induces re-absorption of the bone, (osteoporosis);

it strongly attracts neutrophils and helps them attach themselves to the endothelial cells to extravasate;

it stimulates the macrophagic production of molecules with an oxidizing action;

it is involved in particular pathologies of the Cardio-circulatory System participating in the formation of venous thrombosis, in the pathogenesis of arteriosclerosis and vasculitis;

The TNF is capable of binding itself to two receptors, TNF-R1 (receptor for TNF type 1) and TNF-R2 (receptor for TNF type 2), which are expressed in all somatic cells excluding erythrocytes. In short, the TNF promotes the inflammatory response both systemic and cutaneous, which in turn triggers numerous pathologies also of an auto-immune nature, such as rheumatoid arthritis, Crohn's disease, psoriasis and asthma. Scientific research has so far tried to perfect "biological" drugs (such as, for example, monoclonal antibodies) which inhibit the synthesis of TNF and/or block its receptor.

IL-2:

this is a highly pro-inflammatory, atherogenic cytokine, mainly produced by lymphocytes T, whose synthesis is inhibited by steroids and cyclosporines. IL-2 has a central role in regulating the immunological response: it stimulates in fact the synthesis of IFN in the peripheral leukocytes and induces the production of IL-1 and TNF. IL-2 can also damage the hematoencephalic barrier and integrity of the endothelium of the cerebral vessels, causing neuropsychiatric disorders such as disorientation and depression.

There are consequently numerous pathologies which have been associated with an aberrant production of IL-2, such as Hodgkin's lymphoma, multiple schlerosis, rheumatoid arthritis and Lupus erythematosus.

IL-6:

produced by many cell types above all I.S., with TNF it is amongst the most important members of the group of chemical mediators of the acute phase of the inflammatory process, and is therefore involved in pathologies with a strong inflammatory component, such as asthma (where it participates in the emergence and maintenance of the inflammatory process), chronic intestinal inflammation (Crohn's disease), rheumatoid arthritis and arthrosis. As previously affirmed, in fact, cytokines such as TNF, IL-1 and IL-6 have proved to be greatly involved in the degenerative articular osteoarthrosis process as they have a primary role in regulating the expression of metalloproteases (responsible for cartilage degradation), in the production of prostaglandins and in osteoclastic activation and, for this reason, high cytokine levels have been registered in the synovial fluids of patients suffering from arthrosis and rheumatoid arthritis (R.A.). These discoveries have stimulated the use of inhibitors in the above interleukins and/or receptor antagonists as a new treatment strategy of the arthrosis pathology.

Finally, recent studies have connected cancer with longevity and revealed how some tumors are influenced by the kind of/quantitative situation of the cytokine proteins of the patient: in short, recent evidence has linked a low production profile of IL-10 and high secretion of IL-6 to a deterioration in the clinical survival of patients affected by tumoral pathologies, whereas a genotype capable of producing and maintaining high levels of IL-10 can facilitate survival (Caruso C. et al., Ann N.Y. Acad. SCI., 2004, 1028:1-13).

IL-7:

a cytokine mainly produced by stromal cells of bone marrow, it is also secreted by the thymus and keratinocytes. IL-7 induces the synthesis of inflammatory cytokines such as IL-1, IL-6 and TNF, thus participating in the pathogenesis of some skin diseases (such as psoriasis and cutaneous lymphoma) and the osteoarticular system, high levels of IL-7 have in fact been found in patients suffering from R.A.

IL-12:

this protein also plays a central role in regulating the functions of the I.S. It acts in fact on the differentiation of the lymphocytes, it induces the synthesis of Interferon and TNF, and its production can be inhibited by IL-10. The overproduction of this protein enters in the pathogenesis of diseases of an auto-immune nature such as colitis, arthritis, insulin-dependent diabetes, encephalomyelitis, psoriasis and multiple schlerosis (Brahmachari S. et al., Minerva Med., 2008, 99(2):105-118).

IL-10:

mainly produced by lymphocytes, it is a cytokine of an anti-inflammatory nature, capable of inhibiting the synthesis of IL-2 and Interferon produced by lymphocytes T. The anti-inflammatory action of IL-10 is also revealed in the capacity of inhibiting the synthesis of IL-1, IL-6, IL-8, IL-12 and TNF in the macrophages stimulated with bacterial endotoxins. IL-10 deficiencies are associated with pathologies such as diabetes mellitus and chronic intestinal inflammations, such as Crohn's disease. Recent evidence has led IL-10 to also be experimented as a new therapeutic approach for the treatment of Lupus erythematosus. Low IL-10 levels have been observed in cutaneous tissues of patients suffering of pathologies such as vitiligo, psoriasis, eczema and dermatitis. It should be noted that both corticosteroids and cyclosporine increase the production and/or release of this interleukin from the relative competent cells during conventional immunosuppression therapy for the treatment of inflammations and organ rejection (Zhou X. Et al., Current Drug Targets-Immune, Endocrine & Metabolic Disorders, 2005, 5(465475). Experimental data have also demonstrated its effectiveness in reducing the release of prostaglandins and cyclo-oxygenase induced in vitro by TNF on human synoviocytes, thus indicating the capacity of IL-10 of reducing inflammatory processes which involve articulations affected by osteoarthrosic degeneration (Alaaeddine N. et al., Arthritis & Rheumatism, 1999, 42:710-718). Recent studies have confirmed its therapeutic effectiveness towards the asthma pathology in experimental animal models of bronchial hyper-reactivity, showing how this cytokine has a high therapeutic potentiality in reducing the inflammation which characterizes the air passages of asthmatic patients, in which high concentrations of TNF, IL-1, IL-5, IL-6 and IL-8 have been found in the bronchial-washing liquid and/or on a serum level and/or tissue level (Stankiewicz W. et al., Mediators of Inflammation, 2002, 11:307-312). For this interleukin, the important role of regulator cytokine of the maintenance of immunological homeostasis, has therefore been assumed.

Asthma can be an extremely invalidating disease of which approximately 200 million people in the world suffer, with over 5,000 deaths per year. It is a pathology which is based on a distorted response of the I.S. to environmental factors, consequently linked to an exacerbated production of pro-inflammatory cytokines for the growth and differentiation of mast cells and eosinophils with other types of cells of the I.S. The causes of this out-of-balance activity of the immune system are still not completely known, there are however genetic, environmental, viral and also nutritional factors which contribute in different ways to the development of this pathology. Consequently, finding an effective therapy (systemic and/or local therapy) for its prevention and/or treatment which allows the suspension or reduction of the use of steroids (conventional treatment therapy), could represent a valid solution for both the more serious forms (as it would in any case enable a reduction in the use of steroids) and for less serious cases, as the suspension of the steroid therapy could be total.

BRIEF DESCRIPTION OF THE DRAWINGS

FIG. 10 is a table showing the experimental results of Example 13.

FIG. 11 is another table showing the experimental results of Example 13.

DETAILED DESCRIPTION OF THE INVENTION

Figure 1:
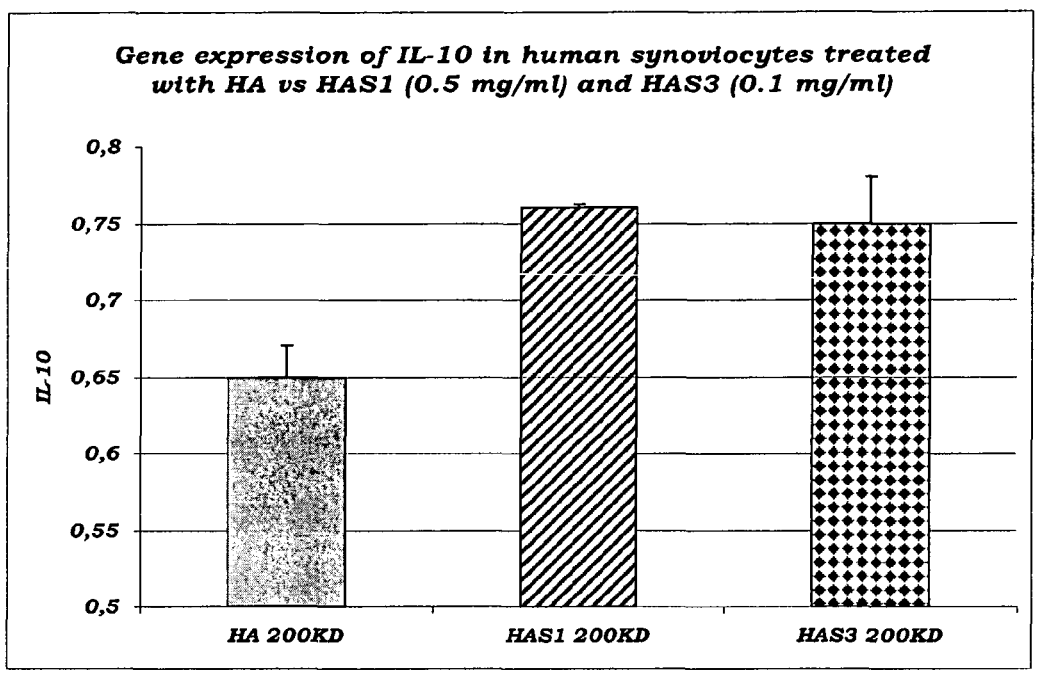
FIG. 1 shows the gene expression of IL-10 in human synoviocytes treated with HA versus HAS1 (0.5 mg/ml) and HAS3 (0.1 mg/ml) as provided in Example 8.

An object of the invention is the new and surprising topic use of HAS as regulator agent of the cytokine activity, as the Applicant has discovered its exclusive capacity in modulating the activity of particular cytokines, it has studied its action mechanism and revealed the substantial difference between the various types of sulfated products known in the state of the art, but above all the Applicant has discovered an unexpected activity vs different types and strains of Herpes virus, Cytomegalovirus and the virus of vesicular stomatitis. Finally, a further object of the present invention relates to the use of HAS as promoter of the skin absorption of drugs of a prevalently anti-inflammatory nature, as a fibrinolytic agent and also as a highly hydrating agent for the treatment therapy of all skin pathologies characterized by dryness, irritation and redness, inflammation and desquamation.

The sulfated hyaluronic acid suitable for the purposes of the present invention is prepared according to the process described in EP 702699 B1: the sulfation is effected by means of the complex $SO_3$-pyridine and involves the alcohol hydroxyls present in the polysaccharide chain starting from a HA deriving from any source, for example, by extraction from cockscombs, either fermentatively or biotechnologically, and having a molecular weight ranging from 400 to $3\times10^6$ Da, in particular from $1\times10^4$ Da to $1\times10^6$ Da, even more in particular from 10,000 to 50,000 Da, 150,000 to 250,000 Da and 500,000 to 750,000 Da.

The derivative obtained maintains all the physical characteristics of the starting polymer unaltered, in particular the molecular weight of the starting HA is not reduced by the sulfation process thus allowing all the physico-chemical characteristics of the starting polysaccharide to be maintained. The sulfation involves the various hydroxyl groups of the disaccharide unit and it is therefore possible to obtain different sulfation degrees, from 0.5 to 3.5 (intended as the number of sulfate groups per disaccharide unit), by varying the quantity of $SO_3$-pyridine introduced as known in the state of the art.

The derivative used in all the experimentations effected generally has sulfation degree 1 or degree 3 and is defined hereafter as HAS1 and HAS3. All the free carboxyl groups of the HA can be salified with cations of an organic and/or inorganic origin.

Both degrees of HAS are soluble in water and they can also be sterilized with the normal techniques known to experts in the field, even if sterilization using an autoclave is preferable.

The Applicant describes and claims the new use of HAS for the preparation of a medicine for topic use:

for the prevention and/or treatment of skin pathologies associated with immune deficiency and, in particular, deficiency of IL-10, such as vitiligo, eczema, psoriasis and dermatitis in general, stimulating the synthesis of anti-inflammatory cytokines;

for the prevention and/or topic treatment of asthma, associated with the activation of IL-1, IL-6 and TNF by inhalation;

for the prevention and/or treatment of skin pathologies associated with damage to the endothelium and/or wall of blood vessels due, for example, to traumas, vascular hemorrhages of a surface nature and/or of medium depth with the consequent formation of clots and edemas;

for the prevention and/or cutaneous treatment of skin diseases associated with the increase/activation of IL-1, IL-2, IL-6, IL-7, IL-8, IL-12 and TNF such as, for example, dermatitis, atopic dermatitis, psoriasis, vitiligo, photodermatitis, urticaria, all skin irritations (also gingival) and eczema;

for the prevention and/or treatment of diseases of an autoimmune nature such as psoriasis, asthma and skin manifestation of systemic (LES) and discoid Lupus erythematosus;

for the prevention and/or topic treatment of skin neoplasias such as, for example, basalioma, Kaposi sarcoma, squamous cell carcinoma, cutaneous lymphoma, mycosis fungoides and actinic keratosis;

for the prevention and/or topic treatment of vascular pathologies such as, for example, vasculitis and scleroderma, associated with the activation of TNF, IL-1 and IL-6;

The Applicant has in fact also demonstrated, in the experimentations described hereunder, that:

HAS is capable of both stimulating the production of new mRNA and the protein synthesis of cytokines of an anti-inflammatory nature (such as, for example, IL-10), thus increasing the immune defense capacity of the cells and consequently the whole organism. The anti-inflammatory action of the above cytokines is revealed in the capacity of inhibiting the synthesis of IL-1, IL-6, IL-8, IL-12 and TNF, all highly pro-inflammatory proteins involved in numerous skin pathologies.

HAS is effective in both diminishing the synthesis of new mRNA and in significantly reducing the protein synthesis of IL-2, IL-7 and IL-12, in situations in which an immune response is not solicited and in particular events of inflammatory stress in which the cells respond by producing a cytokine cascade: especially in this case, the data presented reveal the greater effect of HAS.

HAS is effective in inhibiting the binding of TNF, IL-1 and IL-6 to their receptor. These results are of fundamental importance as they prove that the behaviour of the sulfated product is completely analogous to that of monoclonal antibodies specific for the receptors of the above pro-inflammatory proteins, capable therefore of blocking their function, but at the same time not having this antibody specificity. This receptor blockage represents the most effective way of antagonizing the pro-inflammatory and tumoral effects of the TNF, IL-1 and IL-6 factor, thus opening up new horizons for clinical experimentation, allowing the perfectioning of new therapeutic approaches in the treatment and/or prevention of an extremely large number of pathologies, considering the role that TNF, IL-1 and IL-6 play in the emergence and progression of numerous systemic and skin diseases.

The Applicant also describes and claims the new use of HAS for the preparation of a medicine for topic use:
for the prevention and/or treatment of Herpes Simplex labialis and Herpes genitalis;
for the prevention and/or treatment of the virus of vesicular stomatitis;
for the prevention and/or treatment of Cytomegalovirus.

The Applicant has in fact demonstrated, in the experimentations described hereunder, the powerful anti-viral action of HAS vs different types of virus:

Experimental data prove the antiviral action of HAS1 and HAS3 vs Herpes Simplex virus 1 and 2 and vs the virus of vesicular stomatitis (VSV). The first form, extremely widespread, is responsible for the appearance of characteristic febrile vesicles which normally affect the facial cutis (lips, nostrils); it is also called herpes simplex labialis. The infection caused by herpes labialis can easily reappear as the virus survives inside the cells and is not even eliminated with the use of effective drugs. The second form is a genital infection, also known as herpes genitalis. Both are caught by physical or sexual contact. Due to the location of the virions in the nervous ganglia, where they can remain quiescent for a long period of time, the herpetic infection has recurring characteristics in correspondence with stressing events of the immune system and usually reappears in the primary site. The virus of vesicular stomatitis is an RNA-virus, it strikes mammals (eliminare tutta la parentesi) and is used in the laboratory for studying the development of the life-cycle of the RNA-virus. A comparison between HA-NS1 and HAS1 shows once again that not all sulfated hyaluronic acids are equivalent, as HA-NS1 has proved not to be active at all, whereas both HAS 1 and 3 show a very strong antiviral activity vs Herpes Simplex and also vs VSV. None of the samples tested prove to be cytotoxic towards the host cell, the minimum cytotoxic concentration obtained, in fact, is equal to that of reference drugs normally used in clinical practice for the treatment of Herpes, and on an average has proved to be 100 times higher than that revealed active in the inhibition of viral replication.

Experimental data obtained for both HAS1 and HAS3 have revealed a clear and significant antiviral result vs Cytomegalovirus: this is a particular type of virus which enters some types of cells of our organism in which it reproduces itself parasitically causing their death. It belongs to the same family as herpes labialis and herpes genitalis, chickenpox and infective mononucleosis. Epithelial cells, mucous membranes, lymphonodes are the site of multiple primary infection. It remains in latent form for life in the peripheral blood, in the epithelium of the renal tubules and in the epithelium of the salivary glands. Serious forms are found in immunocompromised subjects (such as those affected by AIDS and transplant subjects in immunosuppressive therapy). The treatment therapy consists in the administration of drugs such as ganciclovir, valganciclovir and foscarnet (inhibitors of the synthesis of viral DNA). Also in this case, HA-NS1 has proved to be non-active in inhibiting the proliferation of the virus confirming the absolute diversity, as anti-viral capacity, between the two types of sulfated products.

A further object of the present invention relates to the use of HAS as a fibrinolytic agent for the degradation of fibrin clots which are formed on a cutaneous level (surface and/or in depth) following the breakage of the endothelium and/or wall of the capillaries and/or small vessels, due to mechanical traumas and/or hemorrhages of a medium/small entity.

In the experimentations described hereunder, the Applicant has in fact demonstrated:
that HAS is effective as Plasmin in the fibrinolysis/debridement of clots and thrombi. Plasmin is an important enzyme belonging to the group of hydrolases capable of degrading many proteins of blood plasma, and in particular the fibrin in thrombi and clots. The degradation of the fibrin is called fibrinolysis. A plasmin deficiency can lead to thrombosis, as the thrombi are not adequately degraded. The substantial difference between the anti-coagulating process and fibrinolytic process should be noted: in the former case the anti-coagulating agent must prevent the formation of coagulum, in the latter case, the fibrinolytic agent, on the other hand, must intervene in a situation in which the coagulum is already present, and must therefore be degraded for its total elimination.

A further object of the present invention relates to the new use of HAS as a skin absorption promoter of drugs such as, for example, those of an anti-inflammatory nature and, finally, as a highly dehydrating agent for the treatment therapy of all skin pathologies characterized by dryness, lichenification, irritation, pruritus and redness, inflammation and desquamation.

The Applicant has in fact demonstrated that:
the sulfation of hyaluronic acid substantially increases skin absorption, consequently,
the hydrating power of HAS has proved to be significantly higher than that of non-sulfated HA and therefore causes an important decrease in the roughness of treated skin surfaces with respect to HA and topic control formulations, thus revealing its capacity of effectively treating and protecting skin surfaces characterized by dryness, irritation, lichenification, pruritus and redness, inflammation and desquamation with all the other skin pathologies which make the skin more sensitive to external agents;

HAS is a powerful and effective skin absorption promoter of drugs. The capacity of HAS of penetrating the skin thickness so efficiently is the scientific basis on which this surprising and unexpected new property is founded, which enables its formulation with pharmacological agents of a varying nature, such as for example, of the non-steroid anti-inflammatory (in particular diclofenac, ketoprofene and ibuprofene) or steroid type, hormones, vaso-dilators, cholinergic agents, antibiotics and others, formulated in various forms, preferably as gels, creams or patches for a dermal and/or transdermal absorption.

Finally, the Applicant describes the preparation of various topic pharmaceutical formulations/compositions containing HAS as sole active principle, or in association with other pharmacologically and/or biologically active agents such as, for example, steroids, hormones, proteins, trophic factors, vitamins, non-steroid anti-inflammatory drugs (FANS) such as, for example diclofenac, ketoprofene or ibuprofene or salts thereof, chemotherapy drugs for topic use, antibiotics, anti-viral agents, local anesthetics, anticoagulants and/or fibrinolytic agents, and/or enzymes such as, for example, collagenase and/or hyaluronidase and/or other proteases; it can be formulated with polymers such as hyaluronic acid and its derivatives, carboxymethylcellulose (CMC) and/or other polymers of a natural (such as collagen) or synthetic nature.

The pharmaceutical composition in question can be formulated as an ointment, lipogel, hydrogel, lipstick, cream, vaginal ovules and bougies, foam, mucosal gel, ophthalmic preparations, vaginal douches, mouthwash, patches for dermal and/or transdermal absorption, especially of FANS and hormones, solutions, it can therefore be administered by topic application or by inhalation for the treatment of pathologies of the respiratory system such as asthma, for example.

Particular attention is paid to compositions containing enzymes such as hyaluronidase in the formulation of a medicine for the treatment of skin hematomas, and those containing non-steroid anti-inflammatory drugs or hormones, in the form of gels, creams and patches for the dermal and/or transdermal absorption of the drug.

Some examples of the preparation of HAS degree 1 and 3, pharmaceutical formulations containing it, are provided for purely descriptive and non-limiting purposes, together with the results obtained by experimentation in vitro.

Example 1

Preparation of the Tetrabutylammonium Salt of Hyaluronic Acid (HA) Having an Average Molecular Weight Equal to 200 KD (Ranging from 150,000 to 250,000 Da)

5.00 g of hyaluronic acid sodium salt of a fermentative origin (200 KD) are dissolved in 250 ml of water and the resulting solution is percolated through a glass column pre-filled with 100 cm$^3$ of Dowex resin in the form of tetrabutylammonium (TBA). The eluted solution of HA-TBA salt is collected and freeze-dried. 7.50 g of product are obtained.

Example 2

Synthesis of Sulfated HA Starting from HA Having an Average Molecular Weight of 200 KD and a Sulfation Degree Equal to 3 Sulfate Groups Per Repetitive Unit Method A 10.0 g of the TBA salt of hyaluronic acid having an average molecular weight of 200 KD prepared according to Example 1, are dissolved in 300 ml of dimethylsulfoxide (DMSO); 26.0 g of the complex $SO_3$-pyridine (sulfur trioxide and pyridine, hereafter abbreviated as $PySO_3$) are dispersed in 150 ml of DMSO, and then added to the solution of HA. After 20 hours under mechanical stirring at a temperature of 21° C., the reaction is interrupted by adding 0.1 volumes of water; the raw reaction product is isolated by precipitation after the addition of 2 volumes of ethanol. The solid obtained is dispersed in 150 ml of water and the pH brought to neutrality with NaOH 1 M. The mixture is exhaustively dialyzed against water through a membrane with a cut-off of 12-14,000 Da. The dialyzed product is subjected to freeze-drying. 9.7 g of product are obtained with a sulfation degree equal to 3 sulfate groups per repetitive unit (yield=88%).

Method B 32.0 g of the TBA salt of hyaluronic acid having an average molecular weight of 200 KD prepared according to Example 1, are dissolved in 900 ml of N-Methyl-Pyrrolidone (NMP); 100 g of $PySO_3$ are dispersed in 600 ml of NMP, and then added to the solution of HA. After 20 hours under mechanical stirring at a temperature of 21±1° C., the reaction is interrupted by adding 0.5 volumes of water. The pH initially lower than 2.5, is brought to neutrality by the addition of a mole of NaOH (in solution). The reaction raw product is isolated by precipitation by the addition of 2.5 volumes of methanol and washed with 2 volumes of a methanol/water mixture 8/2. The solid is re-dissolved and exhaustively dialyzed against water using a membrane with a cut-off of 12-14,000 Da. 30.4 g of product are obtained with a sulfation degree equal to 3 sulfate groups per repetitive unit (yield=86%).

Example 3

Synthesis of Sulfated HA Starting from HA Having an Average Molecular Weight of 200 KD and a Sulfation Degree Equal to 1 Sulfate Group Per Repetitive Unit Using the procedure illustrated in Example 1, 10.0 g of TBA salt of HA are prepared, which are dissolved in 350 ml of DMSO. 10.0 g of the complex $PySO_3$ are dispersed in 100 ml of DMSO, and then added to the solution of HA. After 20 hours under mechanical stirring at a temperature of 21° C., the reaction is interrupted by adding 0.1 volumes of water; the raw reaction product is isolated by precipitation after the addition of 2.5 volumes of ethanol. The solid obtained is dispersed in 150 ml of water and the pH brought to neutrality with NaOH 1 moles/l. The mixture is exhaustively dialyzed against water through a membrane with a cut-off of 12-14,000 Da. The dialyzed product is subjected to freeze-drying. 7.54 g of product are obtained with a sulfation degree equal to 1.0 sulfate group per repetitive unit (yield=93%).

Example 4

Synthesis of Sulfated HA Starting from HA Having a Low Molecular Weight (Average MW of 10 KD, Ranging from 5,000 to 30,000 Da) and a Sulfation Degree Equal to 3 Sulfate Groups Per Repetitive Unit Using the procedure illustrated in Example 1, 12.4 g of TBA salt of hyaluronic acid of low-molecular weight are prepared, which are dissolved in 300 ml of NMP. 40 g of $PySO_3$ are dispersed in 100 ml of NMP, and then added to the solution of HA. After 20 hours under mechanical stirring at a temperature of 21° C., the reaction is interrupted by adding 0.5 volumes of water. The pH initially lower than 2.5, is brought to neutrality by the addition of a mole of NaOH 4M. The reaction raw product is isolated by precipitation by the addition of 2.5 volumes of methanol and washed with 2 volumes of a methanol/water mixture 8/2. The solid is re-dissolved and exhaustively dialyzed against water using a membrane with a cut-off of 3,500 Da. 12.0 g of product are obtained with a sulfation degree equal to 3.0 sulfate groups per repetitive unit (yield=85%).

Example 5

Synthesis of Sulfated HA Starting from HA Having a Low Molecular Weight and a Sulfation Degree Equal to 1 Sulfate Group Per Repetitive Unit Using the procedure illustrated in Example 1, 12.4 g of TBA salt of HA are dissolved in 300 ml of DMSO. 16.0 g of $PySO_3$ are dispersed in 100 ml of DMSO and then added to the solution of HA. After 20 hours under mechanical stirring at a temperature of 21° C., the reaction is interrupted by adding 0.1 volumes of water; the reaction raw product is isolated by precipitation after the addition of 2.5 volumes of ethanol. The solid obtained is dispersed in 150 ml of water and the pH brought to neutrality with NaOH 1 moles/l. The mixture is exhaustively dialyzed against water through a membrane with a cut-off of 3,500 Da. The dialyzed product is subjected to freeze-drying. 9.04 g of product are obtained with a sulfation degree equal to 1.0 sulfate group per repetitive unit (yield=90%).

Example 6

Synthesis of Sulfated HA Starting from HA Having a Molecular Weight within the Range of 500-730 KD and a Sulfation Degree Equal to 3 Sulfate Groups Per Repetitive Unit 21.0 g of hyaluronic acid sodium salt of an extractive origin (500-730 KD) are dissolved in 1.5 l of water and the resulting solution is percolated through a glass column pre-filled with 450 cm³ of Dowex resin in the form of TBA. The eluted solution of HA-TBA salt is collected and freeze-dried. 32.0 g of product are obtained, which are dissolved in 1.35 l of NMP; 100 g of $PySO_3$ are dispersed in 650 ml of NMP, and then added to the solution of HA. After 20 hours under mechanical stirring at a temperature of 23±1° C., the reaction is interrupted by adding 0.5 volumes of water. The pH initially lower than 2.5, is brought to neutrality by the addition of NaOH (in solution at a concentration of 4 moles/1). The reaction raw product is isolated by precipitation by the addition of 2.5 volumes of methanol and washed with 3.5 volumes of a methanol/water mixture 8/2. The solid is re-dissolved and exhaustively dialyzed against water using a membrane with a cut-off of 12-14,000 Da. 30.3 g of product are obtained with a sulfation degree equal to 3 sulfate groups per repetitive unit (yield=83%).

Example 7

Synthesis of Sulfated HA Starting from HA Having a Molecular Weight of 500-730 KD and a Sulfation Degree Equal to 1 Sulfate Group Per Repetitive Unit 21.0 g of hyaluronic acid sodium salt of an extractive origin (500-730 KD) are dissolved in 1.5 l of water and the resulting solution is percolated through a glass column pre-filled with 450 cm³ of Dowex resin in the form of TBA. The eluted solution of HA-TBA salt is collected and freeze-dried. 32.0 g of product are obtained, which are dissolved in 1.65 l of NMP; 40 g of $PySO_3$ are dispersed in 350 ml of NMP, and then added to the solution of HA. After 20 hours under mechanical stirring at a temperature of 25±1° C., the reaction is interrupted by adding 0.5 volumes of water. The pH initially lower than 2.5, is brought to neutrality by the addition of NaOH (in solution at a concentration of 4 moles/1). The reaction raw product is isolated by precipitation by the addition of 3.5 volumes of methanol and washed with 3.5 volumes of a methanol/water mixture 8/2. The solid is re-dissolved and exhaustively dialyzed against water using a membrane with a cut-off of 12-14,000 Da. 22.5 g of product are obtained with a sulfation degree equal to 1.0 sulfate group per repetitive unit (yield=87%).

Example 8

Evaluation of the Regulatory Effect of HAS Degree 1 and Degree 3 on the Gene Expression of IL-10 and IL-12

Figure 2:
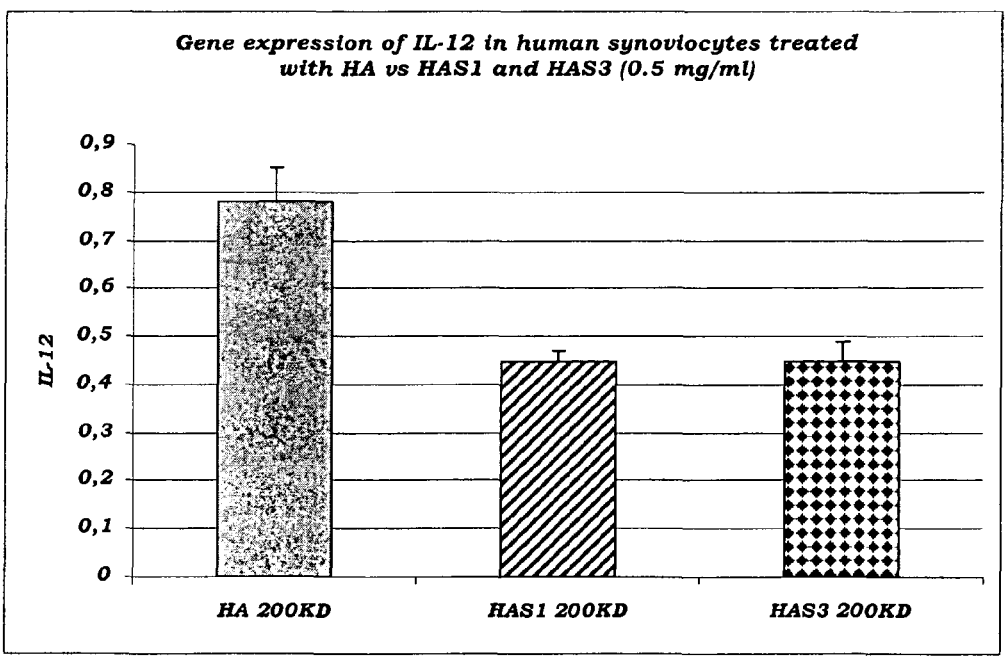
FIG. 2 shows the gene expression of IL-12 in human synoviocytes treated with HA versus HAS1 and HAS3 (0.5 mg/ml) as provided in Example 8.

Human synoviocytes previously expanded in vitro and maintained in a culture at 37° C. with a medium of DMEM containing 10% of FCS, were seeded at a concentration of 20,000 cells per well (synoviocytes are cells capable of producing various types of cytokines, and are therefore normally used for this type of experimental test). Sulfated HA degree 1 (HAS1) and degree 3 (HAS3) prepared as described in Examples 1-3, were then added to the culture medium at concentrations of 0.1 and 0.5 mg/ml (for both samples), whereas the control treatment is represented by non-sulfated HA having an average molecular weight (MW) of 200 KD. After 3 days of treatment, the PCR Real Time was effected to evaluate the gene expression of IL-10 and IL-12: the cell RNA was extracted using the "Trizol" method, following the indications of the supplier (TRIZOL reagent, LIFE Techonologies, GIBCO BRL). In short, the cells were lysed by the addition of 1.0 ml of Trizol and the total RNA was quantified by measuring its absorbance at 260 nm. The appropriate primers were selected for each gene to be amplified, using the software Primer3 (Roche Molecular Diagnostics, Pleasanton, Calif., USA). The gene expression was evaluated by means of PCR Real Time effected with a Rotor-gene TM5500 (Corbett research, Sydney, Australia). The PCR reactions were effected using primers at 300 nm and SYBR Green (Invitroge, Carlsbad, Calif., USA) at 40 cycles of 15 s at 95° C., and 1 min. at 60° C. The value of "Fluorescence thresholds (Ct)" was automatically determined by the software, evaluating an amplification coefficient for the genes studied between 92 and 110%. For each sample of cDNA, the gene expression value was expressed in terms of the ratio between the ct of the house keeping gene (i.e. the gene for the beta-Actin protein which represents the control gene as it is present in every cell and is not subjected to the influence of HAS) and the ct of the gene of interest (i.e. the gene for IL-10 and IL-12), consequently the house keeping ct/gene ct value is indicated in the axis of the ordinates, which therefore indicates the quantity of mRNA expressed by the gene which is being studied. The results obtained are expressed in FIGS. 1 and 2:

FIG. 1: the treatment of human synoviocytes with HAS1 and HAS3 caused a significant increase in the gene expression of the cytokine IL-10 vs the control treated with non-sulfated HA.

FIG. 2:

Also in this experiment, both sulfation degrees (degree 1 and degree 3) of HAS proved to be capable of significantly reducing the gene expression of IL-12, halving the synthesis of its mRNA vs the control treated with non-sulfated HA. The sulfated hyaluronic acid therefore proved to be:

- capable of stimulating the production of new mRNA for the synthesis of anti-inflammatory cytokines, thus increasing the defense capacity of the cell and consequently of the whole organism, vs those pathologies previously described in which IL-10 proved to be of fundamental importance for the resolution and/or improvement of diseases such as asthma, vitiligo and all inflammations in which IL-10 is involved.
- effective in diminishing the synthesis of new mRNA of the highly pro-inflammatory cytokine IL-12, proving to be a valid anti-inflammatory agent capable of intervening on the expression of proteins involved in the pathogenesis of invalidating diseases such as psoriasis and all those previously described.

Example 9

Inhibition of the Binding of TNF to its Receptor Expressed in Monocyte Lines: Evaluation of the Effectiveness of HAS Degree 1 and Degree 3 at Different MW Values These experiments were effected to evaluate the effectiveness of the samples tested (prepared according to Examples 1-4) on the capacity of inhibiting the binding of TNF to its receptor expressed by cells of the I.S. normally used in vitro for this type of experiment, carried out with iodinated cytokine components for an evaluation in Radio-ligand Binding assays.

The experimental procedure was effected as described in Baglioni C. et al., J Biol Chem, 1985, 260:13395-13397.

In short, the line of human histiocytes of the lymphoma U937 was used, with characteristics of monocytes sensitive to the cytotoxic activity of TNF, expressing its relative receptor. The cells were initially incubated with $^{125}$I-TNF 0.028 nM (carried in water) contemporaneously with the samples to be analyzed (at a concentration of 1 mg/ml which proved to be the lowest concentration which causes the maximum inhibition), in an incubation buffer consisting of 50 mM Tris-HCL pH 7.4, 0.5 mM EDTA, at 4° C. for 3 hours.

At the end of the incubation, the cells were centrifuged with dibutylphthalate/dinonylphthalate 2/1 and the pellet obtained was counted in a γ-counter.

Figure 3:
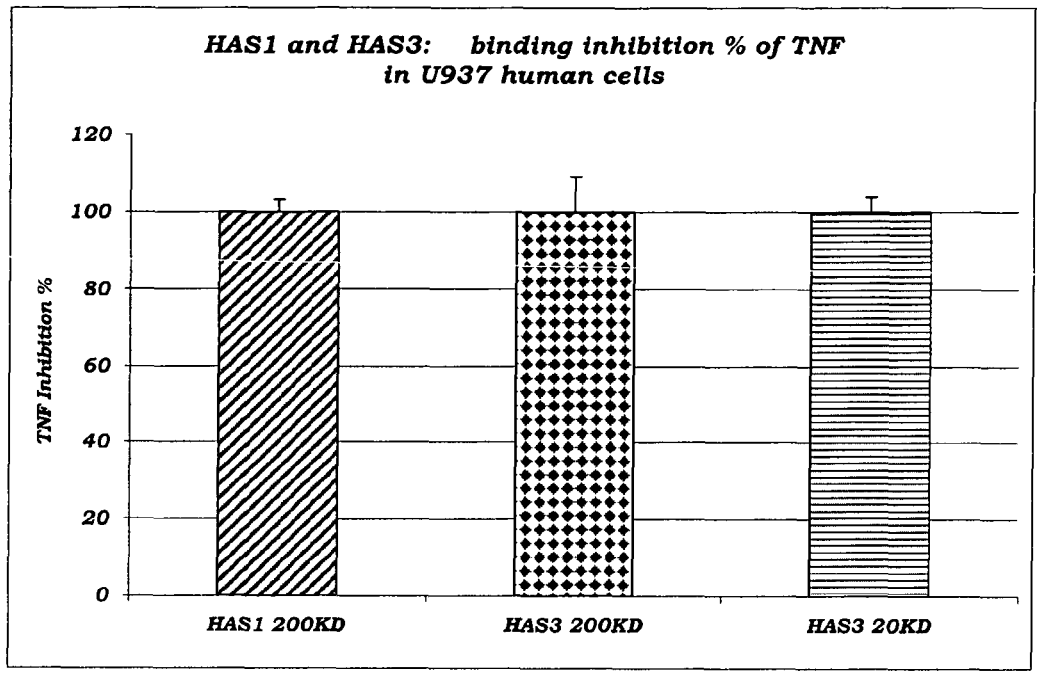
FIG. 3 shows the binding inhibition percentage of TNF in U937 human cells for HAS1 and HAS3 as provided in Example 9.

The results obtained are expressed in FIG. 3:

The results obtained show the effectiveness of HAS in totally (100%) inhibiting the binding of TNF to its receptor, for both degree 1 and degree 3, with a medium and low MW. These results are of fundamental importance as they prove that the behaviour of the sulfated product is completely analogous to that of a monoclonal antibody specific for the TNF receptor, capable therefore of blocking its function. This receptor blockage consequently represents the most effective way of antagonizing the pro-inflammatory and tumoral effects of the TNF factor.

Example 10

Inhibition of the Binding of the Cytokine IL-1 to its Receptor Expressed in Fibroblast Lines: Evaluation of the Effectiveness of HAS Degree 3 at Different MW Values These experiments were effected to evaluate the effectiveness of the samples tested (prepared according to Examples 1-3 and 4) on the capacity of inhibiting the binding of IL-1 to its receptor expressed by 3T3 cells of mouse, normally used in vitro for this type of experiment, carried out with iodinated cytokine components for an evaluation in Radioligand Binding assays.

The experimental procedure was effected as described in Chin J et al., J Exp Med, 1987, 165:70-86.

In short, the line of murine fibroblasts 3T3 was used, sensitive to the cytotoxic activity of IL-1, expressing its relative receptor. The cells were initially incubated with $^{125}$I-IL-1 10 pM (carried in water) contemporaneously with the samples to be analyzed (at a concentration of 1 mg/ml which proved to be the lowest concentration which causes the maximum inhibition), in an incubation buffer consisting of RPMI 1640 containing 20 mM HEPES pH 7.2 and 1% BSA, at 37° C. for 2 hours. At the end of the incubation, the cells were washed with phosphate buffer, then dissolved in 2.5 M of NaOH and counted in a γ-counter.

Figure 4:
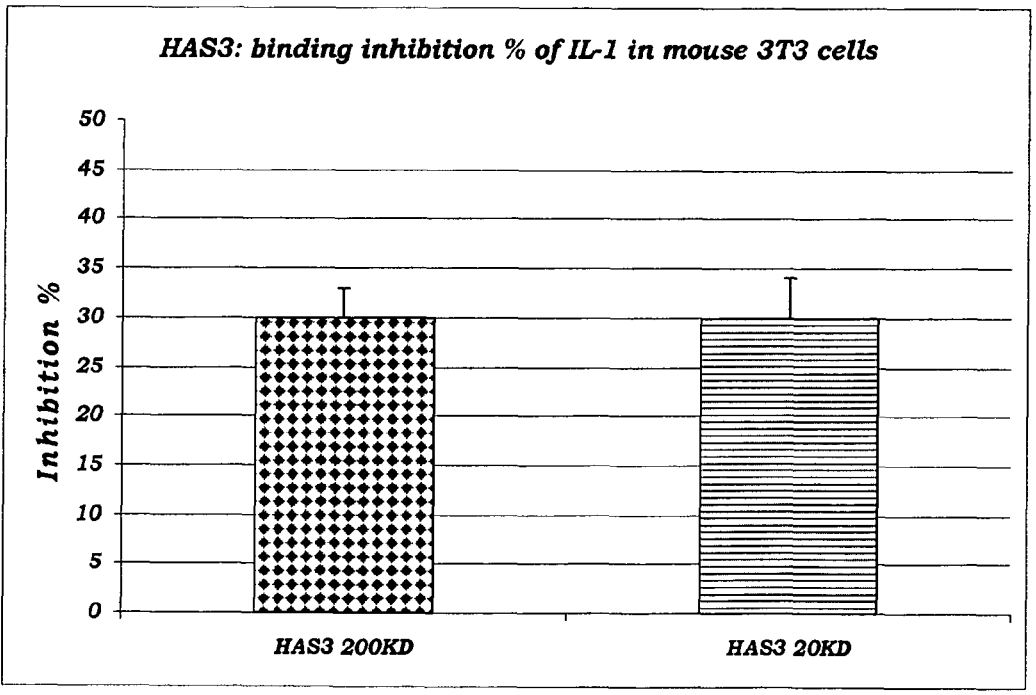
FIG. 4 shows the binding inhibition percentage of IL-1 in mouse 3T3 cells for HAS3 as provided in Example 10.

The results obtained are expressed in FIG. 4:

The results obtained show the effectiveness of HAS (with both medium and low MW) in inhibiting the binding of IL-1 to its receptor at 30%. These results are extremely significant as they prove that the behaviour of the sulfated product is completely analogous to that of a monoclonal antibody specific for the receptor of the cytokine in question, capable therefore of blocking its function. This receptor blockage represents the most effective way of antagonizing the pro-inflammatory and tumoral effects of IL-1, as previously described.

Example 11

Inhibition of the Binding of the Cytokine IL-6 to its Receptor Expressed in Human Myeloma Cells: Evaluation of the Effectiveness of HAS Degree 3 at Different MW Values These experiments were effected to evaluate the effectiveness of the samples tested (prepared according to Examples 1-3 and 4) on the capacity of inhibiting the binding of IL-6 to its receptor expressed in human myeloma U266, normally used in vitro for this type of experiment, carried out with iodinated cytokine components for an evaluation in Radioligand Binding assays.

The experimental procedure was effected as described in Taga T. et al., J Exp Med, 1987, 166:967-981.

In short, the line of human myeloma U266 was used, sensitive to the cytotoxic activity of IL-6, expressing its relative receptor. The cells were initially incubated with $^{125}$I-IL-6 0.08 nM (carried in water) contemporaneously with the samples to be analyzed (at a concentration of 1 mg/ml which proved to be the lowest concentration which causes the maximum inhibition), in an incubation buffer consisting of RPMI 1640 containing 25 mM HEPES pH 7.1 and 10% BSA, at 4° C. for 16 hours. At the end of the incubation, the cells were washed with phosphate buffer, centrifuged at 9,000 rpm and the pellet counted in a γ-counter.

Figure 5:
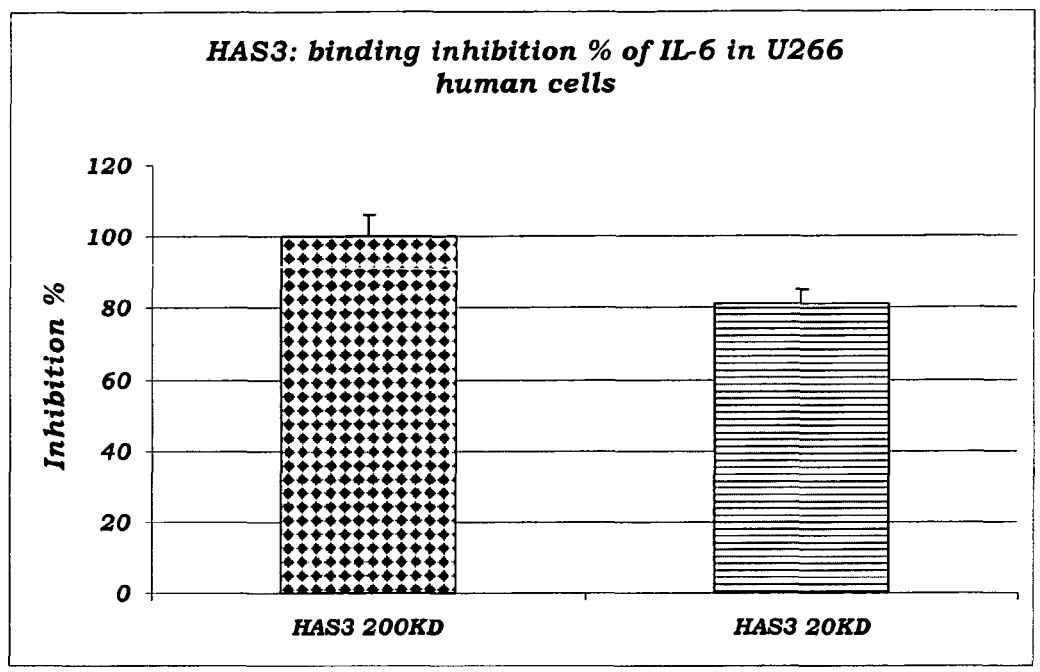
FIG. 5 shows the binding inhibition percentage of IL-6 in U266 human cells for HAS3 as provided in Example 11.
Figure 6:
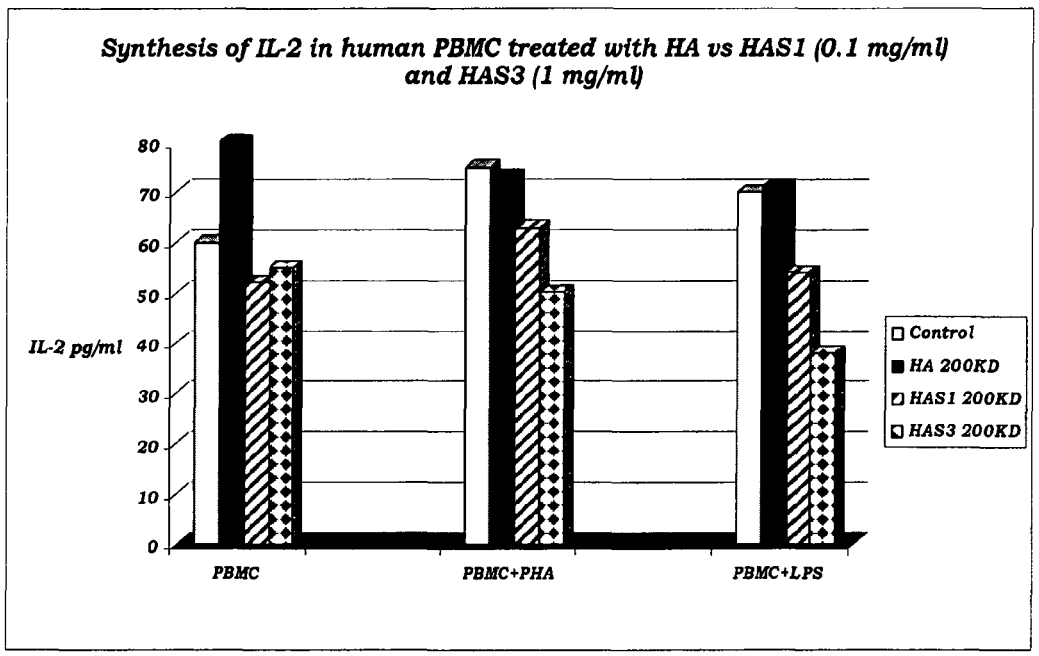
FIG. 6 shows the synthesis of IL-2 in human PBMC treated with HA versus HAS1 (0.1 mg/ml) and HAS3 (1 mg/ml) as provided in Example 12.
Figure 7:
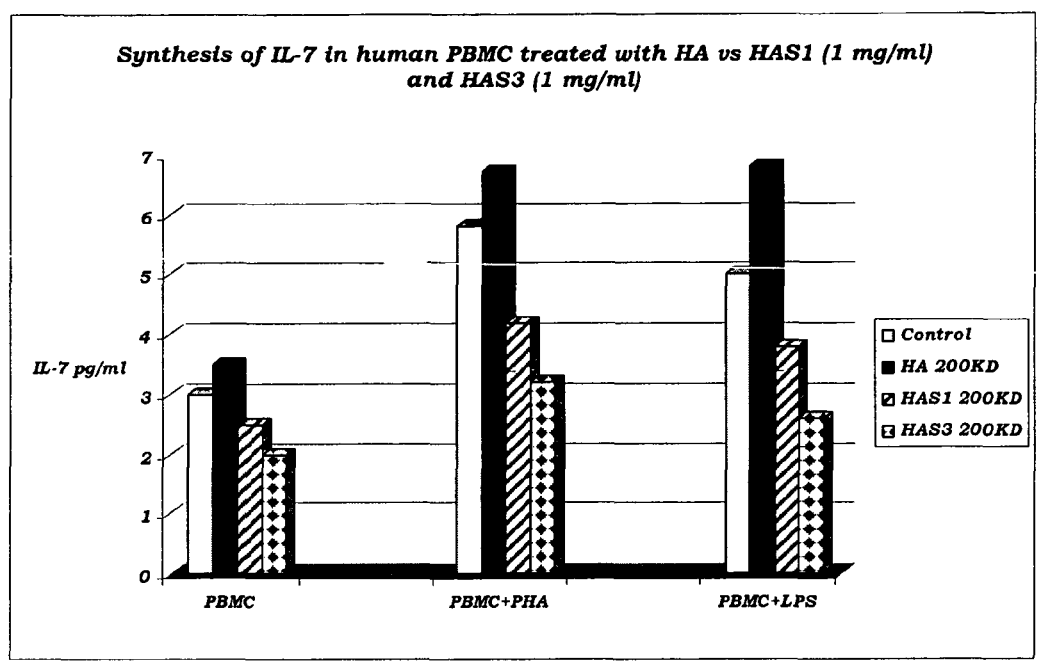
FIG. 7 shows the synthesis of IL-7 in human PBMC treated with HA versus HAS1 (1 mg/ml) and HAS3 (1 mg/ml) as provided in Example 12.
Figure 8:
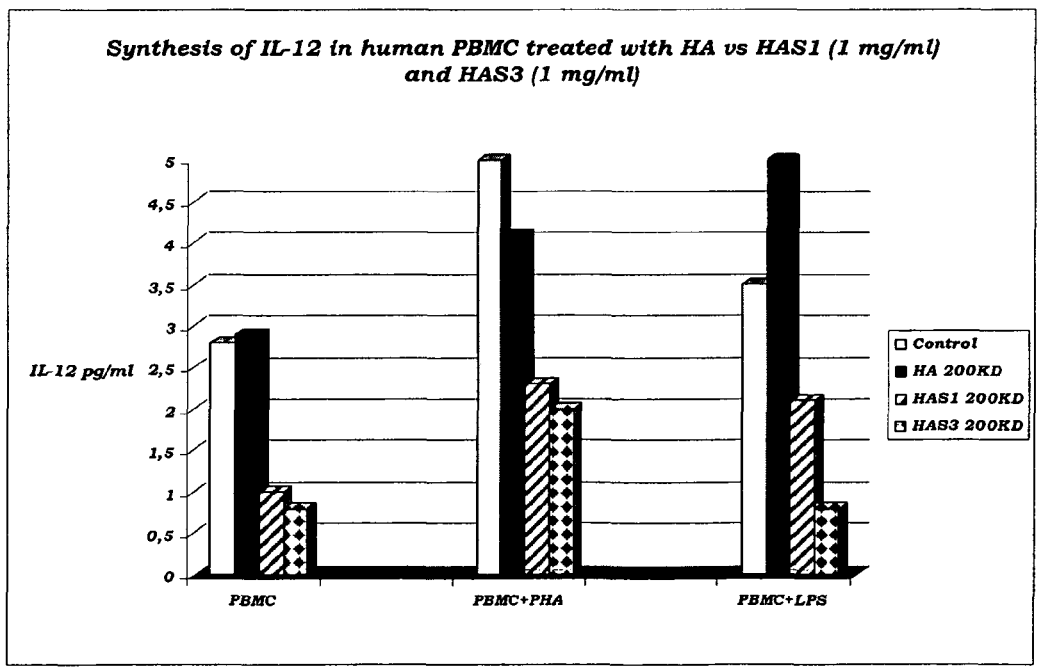
FIG. 8 shows the synthesis of IL-12 in human PBMC treated with HA versus HAS1 (1 mg/ml) and HAS3 (1 mg/ml) as provided in Example 12.

The results obtained are expressed in FIG. 5:

The results obtained show the effectiveness of HAS, with both medium and low MW, in totally (100%) inhibiting the binding of IL-6 to its receptor. These results consequently prove that the behaviour of the sulfated product, also in this case, is completely analogous to that of a monoclonal antibody specific for the receptor of the cytokine in question, capable therefore of blocking its function. This receptor blockage represents the most effective way of blocking the pro-inflammatory effects of IL-6.

Example 12

Evaluation of the Inhibitory Effect of HAS Degree 1 and Degree 3 on the Protein Synthesis of the Cytokines IL-2, IL-7, IL-10 and IL-12 in Human PBMC For these experimentations, mononucleate cells of human peripheral blood (PBMC) were adopted, deriving from various donors for evaluating the effect of HAS on the production of the cytokines listed above, using:
non-sulfated HA (average MW: 200 KD),
HAS1 and HAS3 (prepared as described in Examples 1-3).

The separation of the PBMC (Bøyum A., *Scand J Clin Lab Invest* 21 Suppl, 1968, 97:77-89) was effected using the product Ficoll-Paque PLUS (GE Healthcare) and following the protocol indicated by the supplier. At day zero 100,000 cells were plated per well (using plates with 96 wells) in 200 µl of medium RPMI 1640, to which 10% of fetal bovine serum, HEPES 10 mM, Glutamine 2 mM, 1% Penicillin-Streptomycin 100 U/ml, had been added. The effect of all the samples was evaluated on non-treated PBMC, or stimulated with Lipopolysaccaride LPS (10 µg/ml) (highly pro-inflammatory) or with Phytohemagglutinin PHA (10 µg/ml) (a substance capable of stimulating the lymphocytes to divide themselves), both agents capable of stimulating the synthesis of cytokines. The cells were treated separately with the three compounds at a concentration of 0.1 mg/ml or 1 mg/ml. After 24 hours of incubation at 37° C. (5% $CO_2$), 100 µl of supernatant were taken from each well in order to analyze the production of IL-2, IL-7, IL-10 and IL-12.

The quantification of the inflammation mediators was effected by means of the SearchLight® technology, using a Custom Human 9-Plex Array plate following the protocol indicated by the supplier in the technical card.
The results obtained are expressed in FIGS. 6-9:
These graphs clearly show that HAS degree 1 and degree 3 are capable of significantly reducing the synthesis of IL-2, IL-7 and IL-12 on the part of monocytes, both when the cells are not stimulated and also when, on the contrary, they are stimulated by specific and powerful inflammatory factors and/or mitogens. HAS therefore proves to be a molecule with precise pharmacological characteristics, capable of modulating/regulating the synthesis of cytokines with a marked anti-inflammatory activity, both in situations where an immune response is not stimulated, and in particular inflammatory stress events in which the immune cell responds by producing a cytokine cascade and, above all, in this case, the data presented reveal a greater HAS modulating effect.

Figure 9:
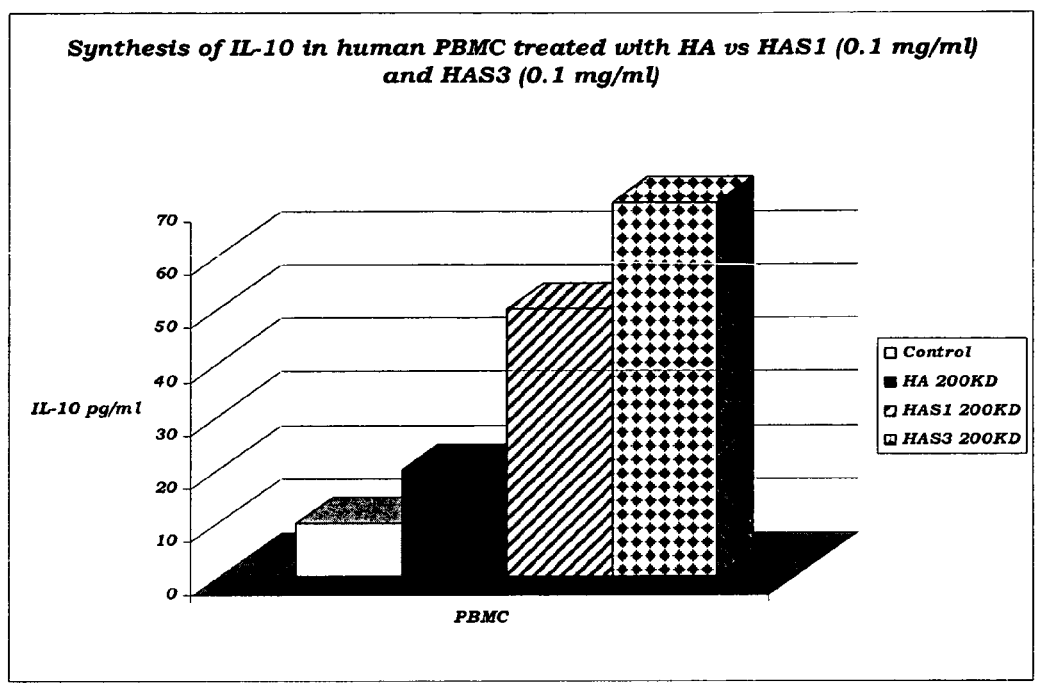
FIG. 9 shows the synthesis of IL-10 in human PBMC treated with HA versus HAS1 (0.1 mg/ml) and HAS3 (0.1 mg/ml) as provided in Example 12.

FIG. 9, on the other hand, confirms the evident stimulus for the production of IL-10 also for cells belonging to the Immune System. It is consequently again confirmed that HAS is capable of modulating the synthesis of cytokines, stimulating those which are anti-inflammatory and inhibiting the synthesis of pro-inflammatory cytokines.

Example 13

Evaluation of the Antiviral Action of HAS Degree 1 and Degree 3 vs HA-NS:
Herpes Simplex Virus-1, Herpes Simplex Virus-2, Vesicular Stomatitis Virus The activity of the samples tested was determined by evaluating the inhibition of the cytopathogenicity caused by the virus of Herpes Simplex Virus-1, (HSV-1: KOS, F and McIntyre strain) and by the virus of Herpes Simplex Virus-2, (HSV-2: G, 196 and Lyons strain) in $E_6SM$ fibroblast cells which derive from muscular/cutaneous embryonic tissue. Furthermore, the anti-viral activity was tested again vs $E_6SM$ cells infected by the virus of vesicular stomatitis (Vesicular stomatitis virus: VSV). HSV-1 is the virus which preferentially infects the oral mucous, whereas HSV-2 attacks the genital mucous. The experimental procedure was effected as described in Baba M. et al., ANTIMICROB. AGENTS CHEMOTHER., 1988, 32:1742-1745.

In short, confluent cell cultures were exposed to infective doses of the viruses listed above in the presence of the samples HS-NS1 (EP0971961), HAS1 and HAS3 prepared as described in Example 1-3. After an incubation period of 1 h at 37° C., the culture medium was substituted with fresh medium only containing the samples to be tested. The cytopathogenicity of the virus was tested on the $2^{nd}$ day of incubation. The measurement of the inhibition of the viral cytopathogenicity was evaluated by determining the inhibition of the synthesis of DNA and RNA in the "infected" cells and subjected to treatment as indicated above: the cells were seeded in micro-wells in a culture medium containing different concentrations of the samples to be tested with 2.5 µCi of 3H-thymidine and 3H-uridine per ml. After 16 h at 37° C., the cells were treated with Trichloroacetic acid, washed in ethanol, left to dry and counted in 7.5 ml of liquid for scintillation. The anti-viral activity of the samples tested is expressed as the minimum concentration required for inhibiting the cytopathogenicity of the virus by 50%: IC50. Furthermore, in order to also evaluate the cytotoxicity of the samples tested, the minimum concentrations necessary for causing morphological damage (observable with an optical microscope) to the cells used, were determined. The comparison was effected vs dextran-sulfate (DS) and the drug Acyclovir (both molecules with a known antiviral effectiveness, therefore used as positive control).

The results obtained are expressed in FIG. 10:
The experimental data confirm the powerful anti-viral action of both HAS1 and HAS3: a comparison between HA-NS1 and HAS1 shows that not all sulfated hyaluronic acids are equivalent as HA-NS1 did not prove to be active, and this difference in efficacy does not depend on the molecular weight or the sulfation degree of hyaluronic acid, it therefore lies in the very structure of HA-NS1 vs HAS1. HAS in fact shows an efficacy equal to that of dextran-sulfate and comparable to that of acyclovir, a reference drug for the treatment of Herpes Simplex. Furthermore, it should be pointed out that acyclovir is inactive vs VSV, whereas HAS degree 1 and 3 has a very powerful anti-viral activity vs VSV.

All the samples tested are non-cytotoxic towards the host cell, the minimum cytotoxic concentration obtained is in fact equal to that of the reference drugs normally used in clinical practice for the treatment of Herpes, and proved to be on an average 100 times higher than that proved active in the inhibition of the viral replication.
Cytomegalovirus The activity of the samples tested was determined by evaluating the inhibition of the cytopathogenicity determined by Cytomegalovirus (CMV: AD-169 and Davis strain) using the previous protocol. The antiviral activity was tested vs HEL cells (pulmonary embryonic cells) and was expressed as the concentration required for inhibiting the number of plaques formed by the above virus by 50%. The results obtained are expressed in FIG. 11:

the table indicates the clear and significant positive result obtained for both HAS1 and HAS3 which again confirms them as effective antiviral agents. Also in this case, HA-NS1 did not prove to be active in inhibiting the proliferation of the virus, confirming the absolute diversity between the two types of degree 1 sulfated product in having an antiviral capacity.

Example 14

Evaluation In Vitro of the Fibrinolytic Properties of HAS Acid Degree 3 with Different MW Values The evaluation of the fibrinolytic properties of the products subjected to the test was compared with the acknowledged fibrinolytic activity of the plasmin. In particular, the dissolution rate of the fibrin network and formation of soluble products of the fibrin degradation (FDP), was evaluated.

The plasma samples used come from whole blood of healthy subjects, without any pharmacological treatment underway.

In order to test the fibrinolytic effectiveness of the products subjected to testing, the blood samples were distributed in various test-tubes in which the clot formation was induced.

The formation of FDP was then evaluated after the addition of:
plasmin, as control treatment
HAS3 prepared according to Example 1 and 2
HAS3 prepared according to Example 4.

Experimental Study

The freshly removed blood samples were distributed in various test-tubes containing sodium citrate in a ratio of 9:1. The test-tubes were immediately centrifuged at 3,000 rpm for 5 minutes. The plasma obtained was transferred to a new test-tube and immediately used for effecting the FDP evaluation.

Thrombin (300 mU/ml), preheated to 37° C. was added to the plasma samples, as activator of the fibrinogen in inducing the formation of the clot.

The following were added to the different cuvettes containing the fibrin clot:
a plasmin solution 0.5 mU, 5 mU, 50 mU, 500 mU and 1 U
solutions of HAS3 at concentrations of 25 mg/ml, 50 mg/ml, 100 mg/ml, 150 mg/ml and 200 mg/ml.

The absorbance variation at 405 nm for 60 sec. was evaluated spectrophotometrically for each cuvette. The reaction was left to proceed until the complete dissolution of the clot.

Coagulated plasma, plasmin solution and a solution of HAS3 200 KD and HAS3 20 KD were mixed in a ratio of 1:1 v/v and maintained at an operating temperature of 37° C.

Table 1. Fibrinolytic Activity of PLASMIN

The table indicates the average mAbs/min values registered in the cuvettes containing coagulated plasma to which plasmin has been added at different concentrations. The values specified indicate the rate at which the fibrin clot is dissolved and consequently the rate at which the FDPs are produced. The fibrinolytic activity of the plasmin is proportional to its concentration.

The average mAbs/min values registered for each concentration of plasmin were subsequently plotted against the respective Units of enzyme to establish the mathematic function which correlates the mAbs/min values with the Units of enzyme.

PLASMIN: Fibrinolytic Activity (mAbs/Min)

TABLE 2

| Fibrinolytic activity of HAS3 at different MW values | | | | |
|---|---|---|---|---|
| 1 U | 500 mU | 50 mU | 5 mU | 0.5 mU |
| 190 | 178 | 126 | 68 | 1 |

The mAbs/min values registered in the cuvettes containing coagulated plasma to which HAS3 had been added at different concentrations, were calculated. The values indicated the rate at which the fibrin clot was dissolved and consequently the rate at which the FDPs were produced. The fibrinolytic activity of HAS3 was proportional to its concentration. In the table, the fibrinolytic activity of HAS3 is expressed as Unit equivalents of Plasmin.

HAS3 (200 KD) Fibrinolytic Activity (Expressed in mU Equivalents of Plasmin)

| 200 mg/ml | 150 mg/ml | 100 mg/ml | 50 mg/ml | 25 mg/ml |
|---|---|---|---|---|
| 1.1 U | 50 mU | 10 mU | 3 mU | 0.5 mU |

HAS3 (10 KD) Fibrinolytic Activity (Expressed in mU Equivalents of Plasmin)

| 200 mg/ml | 150 mg/ml | 100 mg/ml | 50 mg/ml | 25 mg/ml |
|---|---|---|---|---|
| 400 mU | 25 mU | 2 mU | 0.3 mU | 0.25 mU |

Results:

The experimentation effected showed how HAS is a powerful fibrinolytic agent, with an effectiveness equal to Plasmin. Plasmin is an important enzyme, belonging to the group of hydrolases, which degrades many proteins of blood plasma and, in particular, the fibrin of the thrombi and of clots. The degradation of the fibrin is called fibrinolysis. A plasmin deficiency can lead to thrombosis, as the thrombi are not adequately degraded. Although HAS is not an enzyme, it has proved to be equivalently active to enzymatic control, thus allowing the use of the sulfated product as a new fibrinolytic agent, having all the advantages of a non-enzymatic molecule such as, for example, stability at room temperature with much longer preservation times and formulation facility.

Example 15

Evaluation of the Skin Permeation of HAS1 and HAS3 with Different MW Values.
Evaluation of the Skin Absorption of Diclofenac Formulated in Association with HAS Vs HA The skin used for effecting the experiments is obtained from the abdomen of patients between 30 and 50 years old, subjected to surgical abdominal reductions. The sections of skin with a complete thickness are frozen after the surgical intervention and preserved at −20° C. until the moment of the experiment, in which the samples are defrozen at room temperature and accurately separated from the adipose tissue. The skin is divided into square sections of 2.5 cm$^2$, immersed for a minute in water at a temperature of 60° C. and with the help of specific tweezers, the corneal layer and epidermis (SCE) are accurately separated from the underlying tissues. The samples obtained are analyzed with an optical microscope and discarded if punctures are found.

The SCE is assembled in the lower part of a Franz cell with the epidermis facing downwards and the corneal layer in contact with the donor solution which is situated above. The permeation area is a circular surface of 0.636 cm². The lower and upper part of the Franz cell are accurately fixed to the SCE to separate the donor compartment (volume donor solution: 0.50 ml) and acceptor compartment (volume receiver solution 5.00 ml), whose volumes are calibrated exactly. The solvents to be used are degassed in order to eliminate the formation of bubbles, which must be avoided especially for the receiver solution, which is thermostat-regulated at 37° C. by means of a circulating thermostatic bath; under these conditions the SCE is at a temperature of 31-33° C. Each experiment is effected triply and the result is intended as the average of the 3, expressed as quantity of analyte which has crossed the surface unit of skin after 24 hours.

The permeation of HA and HAS1 and HAS3 of both MWs was effected from solutions at 3% (weight/volume), with detection of the permeate quantity through the assay of glucuronic acid and ICP (Inductively Coupled Plasma) spectrometry on sulfur, respectively.

The permeation of sodium diclofenac salt was effected on the salt as such in aqueous solution, on the salt in the presence of HA 200 KD at 3% (weight/volume) and on the salt in the presence of HAS3 prepared according to Example 1-2, at 3% (weight/volume). In all three cases, the concentration of sodium diclofenac salt in the permeating solution is equal to 1% (weight/volume). The concentration of diclofenac was determined through reversephase HPLC analysis on an apparatus Agilent 1200 Series and UV detection (254 nm), C18 column, eluent acetonitrile/water/acetic acid 50/46/4 with a flow of 1.2 ml/min.

Figure 12:
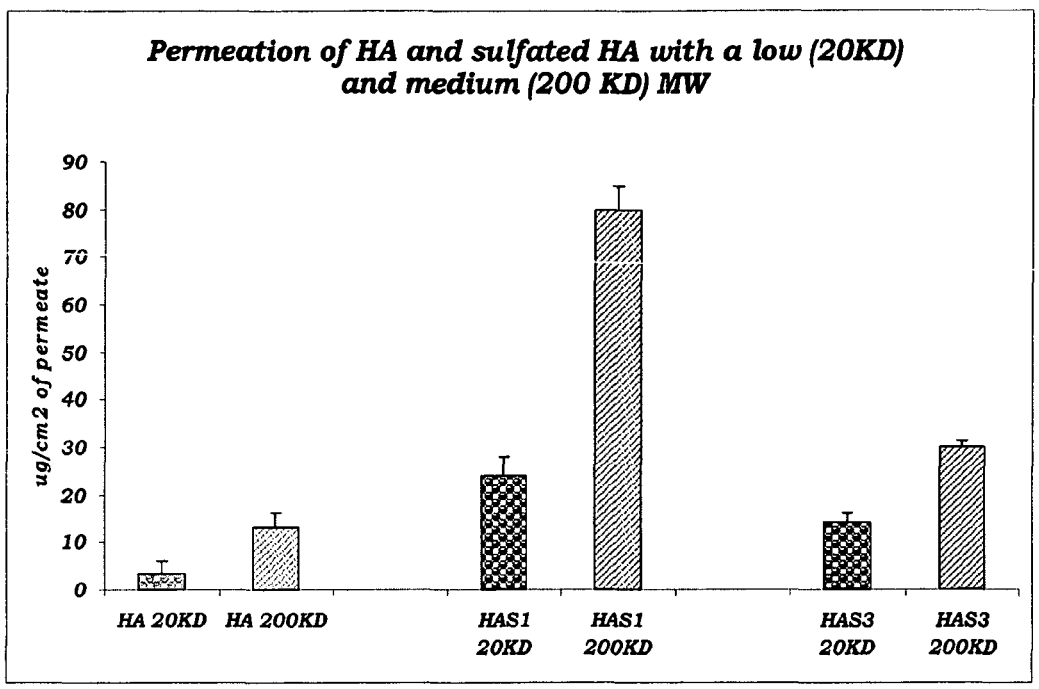
FIG. 12 shows the permeation of HA and sulfated HA with a low (20 KD) and medium (200 KD) MW as provided in Example 15.
Figure 13:
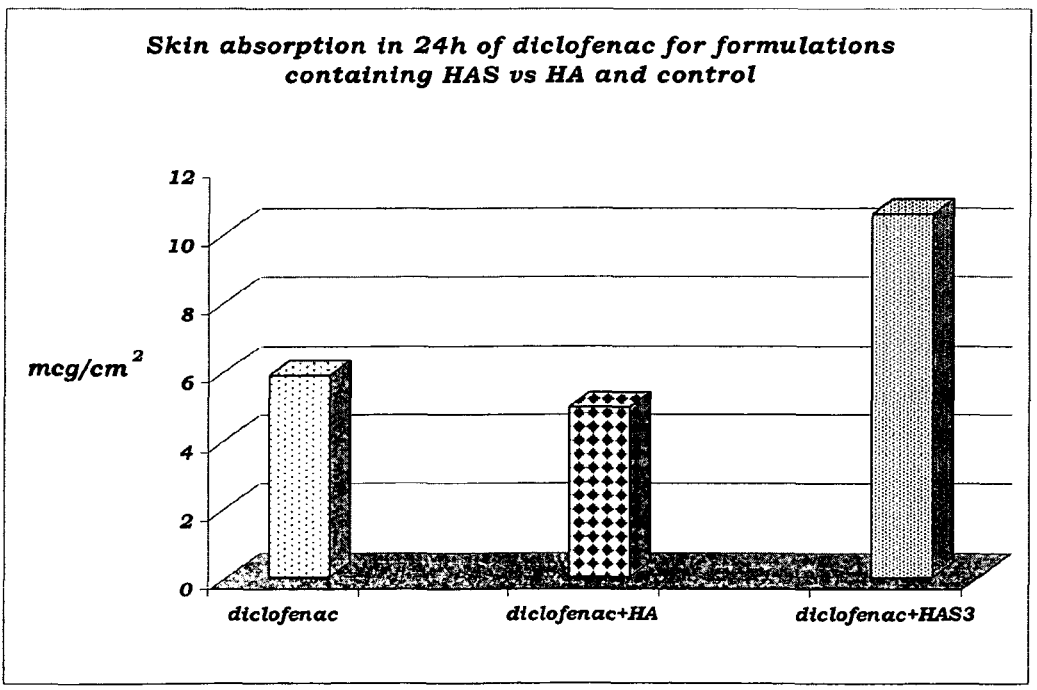
FIG. 13 shows the skin absorption in 24 hours of diclofenac for formations containing HAS versus HA and control as provided in Example 15.

The results obtained are graphed in FIG. 12 and FIG. 13: FIG. 12 shows how the sulfation of HA has significantly increased its permeation through the skin and how this result is particularly evident for the average MW.

FIG. 13, on the other hand, shows how HAS behaves as skin absorption promoter of the active principle diclofenac, doubling its total permeate quantity in 24 h with respect to the control and association with HA.

Example 16

Evaluation of the Hydrating and Protective Activity Obtained with HAS Vs HA and Control Base Cream.

20 human subjects aged between 18 and 70 years, with no skin pathologies and pharmacological treatment underway, were treated daily with certain and constant quantities of the products tested, at the level of the forearm. The experimental products were:
  control: consisting of a hydrating base cream
  base cream (as control) containing HA 200 KD 01%
  base cream (as control) containing HAS3 01%, prepared according to Example 1-2
Cream Base: Composition

|  | DEIONIZED WATER | 85.10% |
|---|---|---|
| DERMOL 88 | ETHYL HEXYL ETHYLHEXANOATE | 6.50 |
| NIKKOMULESE 41 | POLYGLYCERYL-10 PENTASTEARATE BEHENYL ALCOHOL, SODIUM STEAROYL LACTYLATE | 5.00 |
| SEPIGEL 305 | POLYACRYLAMIDE C13-14 ISO-PARAFFIN LAURETH 7 | 2.50 |
| ISOCIDE PF | PHENOXYETHANOL, METHYLPARABEN, ETHYLPARABEN, PROPYLPARABEN, PROPYLENE GLYCOL | 0.50 |
| KEMIPURE 100 | IMIDAZOLIDINYL UREA | 0.30 |
| DISODIUM EDTA | DISODIUM EDTA | 0.10 |

Production Method

Charging 90% water and Disodium Edta and Isocide PF. Heating to 65-70° C.; in an appropriate container dissolving Nikkomulese, Dermol 88 by heating to 65-70° C.; joining the fatty phase to the aqueous phase under the action of a turbine. Cooling to 30-35° C., adding Kemipure 100 dissolved in the remaining 10% of water, adding Sepigel to regulate the viscosity and cooling to 25° C.

The difference in the hydration values obtained was evaluated by means of a corneometer CM825 by an average of 3 points and a profilometric analysis of the skin surface was also effected using a Visioscan VC98 videocamera at time T0 (basal value) and T7, after 7 days of use of the products.

Figure 14:
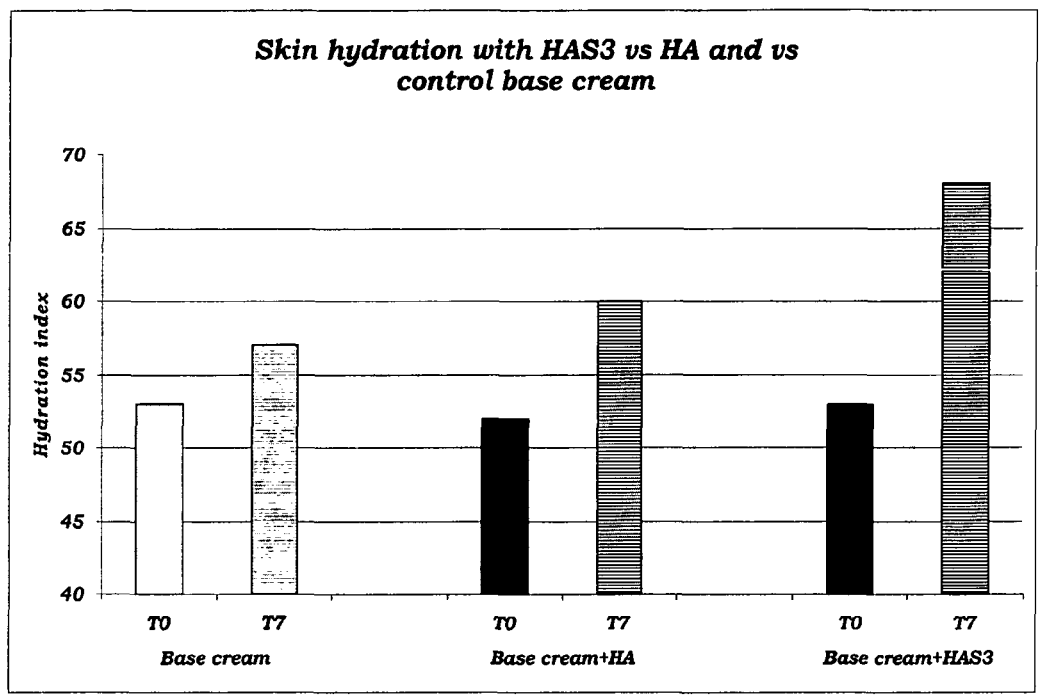
FIG. 14 shows skin hydration with HAS3 versus HA and versus control base cream as provided in Example 16.
Figure 15:
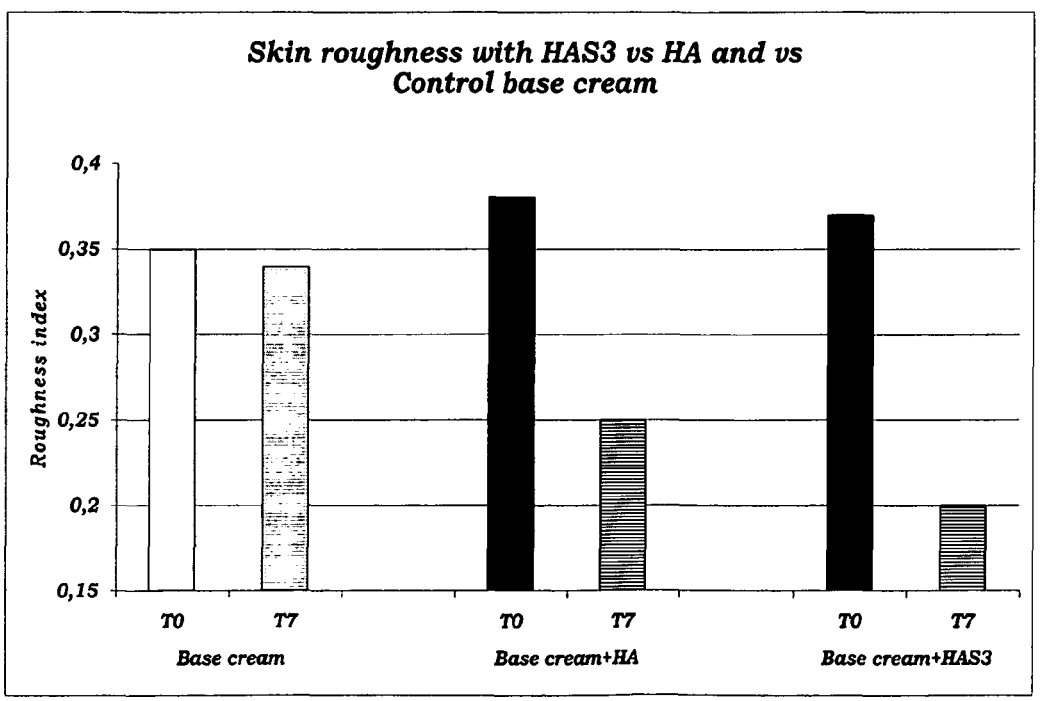
FIG. 15 shows skin roughness with HAS3 versus HA and versus control base cream as provided in Example 16.

The results obtained are graphed in FIGS. 14 and 15: FIG. 14 shows the greater hydrating effect of the skin after treatment with HAS3, vs both the base cream and vs that containing HA. FIG. 15, on the other hand, demonstrates how the skin roughness index, after 7 days of treatment, has significantly diminished with respect to the controls. These data clearly demonstrate the effectiveness of HAS in markedly improving the skin hydration index, showing an efficient hydrating and protective activity on the skin by reducing the transpiration of transepidermal water.

Example 17

Preparation of a Formulation in the Form of a SOLUTION for Inhalations Containing HAS Degree 1

40 mg (or 20 mg if the HAS has a MW of 500-730 KD) of sulfated hyaluronic acid degree 1, having a low or medium MW, are introduced into a 50 ml glass flask, after which 15 ml of PBS 0.2M at sterile pH 7.4, are added. The mixture is subjected to stirring for about 30 minutes, until the complete dissolution of the powder. When the complete dissolution has been obtained, 2 ml of glycol propylene and further PBS 0.2M at sterile pH 7.4 are added until the total volume of 20 ml is reached. The solution is maintained under stirring for a few minutes.

Example 18

Preparation of a Formulation in the Form of a SOLUTION for Inhalations Containing HAS Degree 3

100 mg of sulfated hyaluronic acid degree 3 (HAS3) obtained from HA 200 KD are introduced into a 50 ml glass flask, after which 15 ml of PBS 0.2M at sterile pH 7.4, are added. The mixture is subjected to stirring for about 30 minutes, until the complete dissolution of the powder. When the complete dissolution has been obtained, 2 ml of propylene glycol and further PBS 0.2M at sterile pH 7.4 are added until the total volume of 20 ml is reached. The solution is maintained under stirring for a few minutes.

Example 19

Preparation of a Formulation in the Form of a HYDROPHILIC GEL Containing HAS, HA and CMC Methyl- and propyl-parabene are dissolved in purified water at 80° C. After cooling the solution to room temperature, sodium hyaluronate is added under stirring until dissolution followed by HAS1 (or HAS3), maintaining the stirring until complete dissolution. Glycerol and propylene glycol are then added under stirring until complete dissolution. Sodium carboxymethylcellulose (CMC) is finally added and the mixture is mixed until a gelified solution is obtained.

Example 20

Preparation of a Formulation in the Form of a HYDROPHILIC GEL for Mucosal Use (without Preservatives) Containing HAS and HA Sodium hyaluronate is dissolved under stirring, and then HAS1 (or HAS3) in a quantity of water of about 90% of that envisaged in the formula. Propylene glycol, Symdiol 68 are added followed by MP Diol Glycol, mixing until the complete dissolution of the various components. Carbomer 974P is subsequently added and the stirring is maintained until the homogeneous dispersion of the latter. Beads of sodium hydroxide are dissolved in the remaining 10% of water and this solution is added slowly to the that previously obtained, the mixture is mixed to obtain the gelification of the aqueous phase.

Example 21

Preparation of a Formulation in the Form of a HYDROPHILIC GEL Containing HAS and Hyaluronidase Methyl- and propyl-parabene are dissolved in purified water at 80° C. After cooling the solution to room temperature, the enzyme Hyaluronidase is added under stirring, followed by HAS3, maintaining the stirring until complete dissolution of the two components. Carbomer 974P is subsequently added and the stirring is maintained until the homogeneous dispersion of the latter. TEA is then added to obtain the gelification of the aqueous phase. Glycerol and propylene glycol are finally added under stirring.

Example 22

Preparation of a Formulation in the Form of a HYDROPHILIC CREAM (Emulsion O/A) Containing HAS and Hyaluronidase The oil phase is prepared by melting liquid paraffin, stearic acid and Tefose 1500 under stirring at 50° C. The aqueous phase is prepared separately by the initial dissolution at 80° C. of methyl-parabene and subsequent cooling to room temperature and the final incorporation of glycerol, Hyaluronidase and subsequently HAS3 under stirring until the complete dissolution of the various components.

The aqueous phase is joined to the oil phase and emulsification is effected, the emulsion O/A obtained is cooled under stirring to room temperature.

Example 23

Preparation of a Formulation in the Form of a FOAM Containing HAS and Hyaluronidase Methyl- and propyl-parabene are dissolved in purified water at 80° C. After cooling the solution to room temperature, the enzyme Hyaluronidase is added under stirring, followed by HAS3, maintaining the stirring until complete dissolution. Propylene glycol is then added and the mixture is mixed until complete dissolution; polyvinylpyrrolidone is subsequently incorporated, mixing until complete dissolution and finally polysorbate 80 maintaining the stirring until dissolution.

The distribution phase of the solution obtained is then effected in a cylinder, proceeding with pressurization with a propellant of isobutane, n-butane, propane.

Example 24

Preparation of a Formulation in the Form of an Ointment Containing HAS3 and Hyaluronidase The base ointment is prepared by melting light liquid paraffin and white Vaseline under stirring at 70° C. After cooling to room temperature, Hyaluronidase is incorporated under stirring, followed by HAS3 and the mixture is mixed until a homogeneous suspension is obtained.

Example 25

Preparation of a Formulation in the Form of a LIPOGEL Containing HAS3 and Hyaluronidase Light liquid paraffin, white vaseline and cetylstearyl alcohol are melted under stirring at 90° C. The lipogelifying agent hydrogenated castor oil is added under stirring until a homogeneous solution is obtained and the mixture is then slowly cooled to room temperature. Hyalurondiase, HAS3 are finally incorporated and the mixture is mixed until a homogenous suspension is obtained.

Example 26

Preparation of a Formulation in the Form of a LIPSTICK Containing HAS and HA

The correct quantity of liquid paraffin indicated in the manufacturing formula is charged into a suitable container. It is heated to 88-92° C. and white soft paraffin, hard paraffin, white beeswax, ceresin, arlacel are then added under stirring, the stirring is maintained until the complete melting of the various components. All-raca-tocopheryl acetate, allantoine, butylhydroxytoluene, propyl p-hydroxybenzoate are then incorporated and the mixture is mixed until complete dissolution, maintaining the mass at 88-92° C.

The quantity of purified water envisaged in the formula is charged separately into a suitable container, sodium hyaluronate, HAS1 (or HAS3) are then added under stirring until complete dissolution, followed by Disodium Edetate maintaining the stirring until dissolution.

The aqueous phase is transferred under stirring to the container containing the molten mass, maintaining the system at 88-92° C. and the stirring until a limpid solution is obtained. The two aromatizing agents are then added under stirring and the mixture is mixed for 10'. The molten mass is poured into moulds and is immediately cooled to T<0° C. until solid sticks are obtained.

Example 27

Preparation of a Formulation in the Form of Vaginal Ovules Containing HAS and HA The gelatine is allowed to swell in 70% of purified water at 85° C.; sodium hyaluronate and HAS1 (or HAS3) are dissolved in the remaining quantity of water and this solution is mixed with the glycerine brought to the same temperature. The glycerine solution is added to the swollen gelatine solution and the stirring is maintained until the complete dissolution of the gelatine. The mass is poured into moulds and cooled to T<0° C. until solid ovules are obtained.

Example 28

Preparation of a Formulation in the Form of a HYDROPHILIC CREAM (Emulsion 0/A) Containing HAS and HA The oil phase is prepared by melting liquid paraffin, stearic acid and Tefose 1500 under stirring at 50° C. The aqueous phase is prepared separately by the initial dissolution at 80° C. of methyl-parabene and subsequent cooling to room temperature and the incorporation of glycerol, sodium hyaluronate and subsequently HAS1 (or HAS3) under stirring until the complete dissolution of the various components.

The aqueous phase is joined to the oil phase and emulsification is effected, the emulsion O/A obtained is cooled under stirring to room temperature.

Example 29

Preparation of a Formulation in the Form of an Ointment Containing HAS

The base ointment is prepared by melting light liquid paraffin and white Vaseline under stirring at 70° C. After cooling to room temperature, HAS1 (or HAS3) is incorporated under stirring, and the mixture is mixed until a homogeneous suspension is obtained.

Example 30

Preparation of a Formulation in the Form of a Hydrophilic Gel Containing HAS3, HA and Diclofenac Methyl- and propyl-parabene are dissolved in purified water at 80° C. After cooling the solution to room temperature, sodium diclofenac, sodium hyaluronate and then HAS3 are added under stirring, maintaining the stirring until complete dissolution of the two components. Carbomer 974P is subsequently added and the stirring is maintained until the homogeneous dispersion of the latter. TEA is then added to obtain the gelification of the aqueous phase. Glycerol and propylene glycol are finally incorporated under stirring.

Example 31

Preparation of a Formulation in the Form of a Hydrophilic Cream (Emulsion 0/A) Containing HAS3 and Diclofenac The oil phase is prepared by melting liquid paraffin, stearic acid and Tefose 1500 under stirring at 50° C. The aqueous phase is prepared separately by the initial dissolution at 80° C. of methyl-parabene and subsequent cooling to room temperature and the final incorporation of glycerol, sodium diclofenac and subsequently HAS3 under stirring until the complete dissolution of the various components.

The aqueous phase is joined to the oil phase and emulsification is effected, the emulsion O/A obtained is cooled under stirring to room temperature.

Example 32

Preparation of a Formulation in the Form of a Foam Containing HAS and Diclofenac Methyl- and propyl-parabene are dissolved in purified water at 80° C. After cooling the solution to room temperature, sodium diclofenac is added under stirring, followed by HAS3, maintaining the stirring until complete dissolution. Propylene glycol is then added and the mixture is mixed until complete dissolution; polyvinylpyrrolidone is subsequently incorporated, mixing until complete dissolution and finally polysorbate 80 maintaining the stirring until dissolution.

The distribution phase of the solution obtained is then effected in a cylinder, proceeding with pressurization with a propellant of isobutane, n-butane, propane.

Example 33

Preparation of Formulations in the Form of a Skin Patch Containing HAS and Diclofenac These examples relates to the preparation of a polymeric matrix containing HAS for the controlled release of drugs for topic use, and in this case FANS diclofenac sodium salt, which improves the dermal and/or transdermal absorption of the active principle contained therein, thanks to the promoter action of HAS. The matrix in question preferably comprises copolymers of acrylic acid and its acrylic and/or methacrylic esters with a glass transition temperature (Tg) lower than room temperature, preferably lower than 0° C., whose free carboxyl groups present along the polymer chain are salified with organic bases (for example, ammonia, ethylene diamine, copolymers of acrylic and/or methacrylic acid ester having a cationic ammonium function in the alkyl group (EUDRAGIT® E100 is preferred) or inorganic bases (for example, hydroxides or carbonate or bicarbonate of alkaline, alkaline-earth and transition metals) as is known to experts in the field. The copolymers normally used in accordance with the present invention consist of 2 or more monomers in variable percentages; examples of these monomers are:
  acrylic acid
  butyl and/or methyl acrylate
  2-ethyl hexyl acrylate
  Glycidyl methacrylate
  vinyl acetate Many copolymers are available on the market (such as Duro-Tak® 280-2416, 280-2516, 87-2620, 87-2852, 380-1054, 87-2051, National and Starch) dissolved in organic solvents, with a percentage of free carboxyl groups ranging from 0.1 to 15%, which can be salified with organic or inorganic bases, as described above. These copolymers are preferably contained in the skin patch matrix in an amount of 30-90% by weight.

Furthermore, polymeric matrices containing HAS comprising the following two main components may be prepared:
  a: Polymethacrylates: i.e. copolymers of acrylic and/or methacrylic acid ester having a cationic ammonium function in the alkyl group (EUDRAGIT® E100, EUDRAGIT® RS and EUDRAGIT® RL) are preferred. Said polymers may constitute from 10 to 40% by weight of the total of adhesive matrix after drying, preferably from 10 to 25%.
  b: organic dicarboxylic or tricarboxylic acid (such as, for example, succinic, fumaric, adipic and lauric acid), as counterion to the cationic component a, (in addition, they act as reticulating agents of component a). Component b can be adjusted so that partial or complete neutralization is affected. A further suitable component b are acid-funtional acrylate or methacrylate polymers, for example, polyacrylic acid Carbopol®. Components b may be contained in % in weight ranging from 1 to 40% of the total of the adhesive formulation after drying, preferably from 1 to 20%.

The above polymeric matrix within the final formulation is within the range of 10-90% with respect to the dry weight, preferably from 50 to 90% based on dry weight of the final composition. The quantity of active principle incorporated varies in relation to its nature and the desired dermal or transdermal therapeutic effect. It is normally present in a quantity ranging from 0.1 to 30% by weight with respect to the dry weight of the final composition.

The formulation can also contain excipients, lenitives, emollients, emulsifying agents, adhesion modulators, preservatives, plasticizers, acidifiers/buffers. The amounts of the excipients may vary in great ranges, between 0.01 and 30% depending on their function.

A skin absorption promoter with lenitive, antipruritic and anti-reddening properties is HAS degree 1 or degree 3, preferably degree 3, present in concentrations ranging from 0.1 to 30% of the dry weight of the final composition. The above matrix ensures: a controlled, constant permeation of the active principle without irritation, and adhesiveness to the skin.

Preparation Method 1 kg of the methacrylate copolymer selected (for example, Duro-Tak® 280-2416, 280-2516 or 87-2852) having a content solid of 30-40% w/w, is added under mechanical stirring with 300 g of a 30% w/w EUDRAGIT® E100 water/solvent based solution; the mixture is left under moderate stirring for 30 min. Thereafter, the active principle (100 g of sodium diclofenac salt) and HAS3 previously dissolved in an aqueous solution, are then added. The mixture is left under stirring until the complete dissolution. For the preparation of the matrix layer, this mixture is then laid on top of a film of silicon polyester/paper and drying is effected by evaporation of the residual solvents. The spread matrix has a dry weight of about 60 g/m². The matrix thus obtained is then coupled with a non-woven polyester fabric or polyethylene film for the final formation of the patch.

The final composition of each single patch contains 140 mg of diclofenac and 40 mg of HAS3.

TABLE

| Components | Quantity (mg/1 g of hydrogel) |
|---|---|
| HYDROPHILIC GEL (Example 19) | |
| HAS1 (HAS3) | 40 mg (10 mg) |
| CMC | 20 mg |
| Glycerol | 100 mg |
| Propylene Glycol | 66.75 mg |
| Sodium Hyaluronate | 2 mg |
| Methyl p-hydroxybenzoate | 2 mg |
| Propyl p-hydroxybenzoate | 0.2 mg |
| Purified Water | up to 1 g |
| HYDROPHILIC GEL for mucosal use (Example 20) | |
| HAS1 (HAS3) | 10 mg |
| Carbomer 974P | 15 mg |
| Propylene Glycol | 100 mg |
| Sodium Hydroxyde | 0.33 mg |
| Sodium Hyaluronate | 2 mg |
| MP-Diol Glycol | 37.5 mg |
| SymDiol 68 | 90 mg |
| Purified Water | up to 1 g |

| Components | Quantity (U.I or mg/1 g of hydrogel) |
|---|---|
| HYDROPHILIC GEL (Example 21) | |
| HAS3 | 10 mg |
| Hyaluronidase | 150 U.I |

TABLE-continued

| | |
|---|---|
| Carbomer 974P | 15 mg |
| Glycerol | 100 mg |
| Propylene Glycol | 66.75 mg |
| Triethanolamine | 13.25 mg |
| Methyl p-hydroxybenzoate | 2 mg |
| Propyl p-hydroxybenzoate | 0.2 mg |
| Purified Water | up to 1 g |

| Components | Quantity (U.I or mg/1 g of cream) |
|---|---|
| HYDROPHILIC CREAM (Emulsion O/A) (Example 22) | |
| HAS3 | 10 mg |
| Hyaluronidase | 150 U.I |
| Tefose 1500 | 110 mg |
| Glycerol | 80 mg |
| Stearic Acid | 33 mg |
| Liquid Paraffin | 40 mg |
| Methyl p-hydroxybenzoate | 1 mg |
| Purified Water | up to 1 g |

| Components | Quantity (U.I or mg/1 g of solution) |
|---|---|
| FOAM (Example 23) | |
| HAS3 | 10 mg |
| Hyaluronidase | 150 U.I |
| Polysorbate 80 | 40 mg |
| Propylene Glycol | 40 mg |
| Polyvinylpyrrolidone | 30 mg |
| Methyl p-hydroxybenzoate | 2 mg |
| Propyl p-Hydroxybenzoate | 0.3 mg |
| Purified Water | up to 1 g |
| A cylinder contains about 94% of solution and 6% of propellant (isobutane, n-butane, propane) | |

| Components | Quantity (U.I or mg/1 g of ointment) |
|---|---|
| OINTMENT (Example 24) | |
| HAS3 | 20 mg |
| Hyaluronidase | 200 U.I |
| Light Liquid Paraffin | 200 mg |
| White Petrolatum | up to 1 g |

| Components | Quantity (U.I or mg/1 g of Lipogel) |
|---|---|
| LIPOGEL (Example 25) | |
| HAS3 | 20 mg |
| Hyaluronidase | 200 U.I |
| Hydrogenated Castor Oil | 10 mg |
| Cetostearyl Alcohol | 50 mg |
| White Petrolatum | 365 mg |
| Light Liquid Paraffin | up to 1 g |

| Components | Quantity (mg/1 g lipstick) |
|---|---|
| LIPSTICK (Example 26) | |
| HAS1 (HAS3) | 30 mg (10 mg) |
| Liquid Paraffin | 253.2 mg |
| White Soft Paraffin | 326.2 mg |
| Hard Paraffin | 144.3 mg |
| Beeswax white | 96 mg |
| Ceresin | 28.2 mg |
| Arlacel 582 | 95.8 mg |
| Sodium Hyaluronate | 2 mg |
| Allantoin | 1.1 mg |
| all-rac-a Tocopheryl Acetate | 1.1 mg |
| Propyl p-hydroxybenzoate | 0.4 mg |
| Butylhydroxytoluene | 0.4 mg |
| Purified Water | 19.2 mg |
| Disodium Edetate | 1.1 mg |

TABLE-continued

| | |
|---|---|
| Vanilla Flavour | 0.5 mg |
| Sweet Flavour | 0.5 mg |

VAGINAL OVULES (Example 27)

| Components | Quantity (mg/1 g of ovule) |
|---|---|
| HAS1 (HAS3) | 10 mg |
| Glycerin | 580 |
| Gelatin | 200 |
| Sodium Hyaluronate | 2 |
| Purified Water | up to 1 g |

HYDROPHILIC CREAM (Emulsion O/A) (Example 28)

| Components | Quantity mg/1 g of cream) |
|---|---|
| HAS1 (HAS3) | 10 mg |
| Tefose 1500 | 110 mg |
| Glycerol | 80 mg |
| Stearic Acid | 33 mg |
| Sodium Hyaluronate | 2 mg |
| Liquid Paraffin | 40 mg |
| Methyl p-hydroxybenzoate | 1 mg |
| Purified Water | up to 1 g |

OINTMENT (Example 29)

| Components | Quantity (mg/1 g of ointment) |
|---|---|
| HAS1 (HAS3) | 20 mg |
| Light Liquid Paraffin | 200 mg |
| White Petrolatum | up to 1 g |

HYDROPHILIC GEL (Example 30)

| Components | Quantity (mg/1 g of hydrogel) |
|---|---|
| Diclofenac sodium (*) | 30 mg |
| Carbomer 974P | 15 mg |
| Glycerol | 100 mg |
| HAS3 | 20 mg |
| Sodio Ialuronato | 2 mg |
| Propylene Glycol | 66.75 mg |
| Triethanolamine | 13.25 mg |
| Methyl p-hydroxybenzoate | 2 mg |
| Propyl p-hydroxybenzoate | 0.2 mg |
| Purified Water | up to 1 g |
| (*): sodium diclofenac 3% | |

HYDROPHILIC CREAM (Emulsion O/A) (Example 31)

| Components | Quantity (mg/1 g of cream) |
|---|---|
| Diclofenac sodium | 10 mg |
| Tefose 1500 | 110 mg |
| Glycerol | 80 mg |
| HAS3 | 30 mg |
| Stearic Acid | 33 mg |
| Liquid Paraffin | 40 mg |
| Methyl p-hydroxybenzoate | 1 mg |
| Purified Water | up to 1 g |
| (*): sodium diclofenac 1% | |

FOAM (Example 32)

| Components | Quantity (mg/1 g of solution) |
|---|---|
| Diclofenac sodium | 40 mg |
| Polysorbate 80 | 40 mg |
| Propylene Glycol | 40 mg |
| HAS3 | 10 mg |
| Polyvinylpyrrolidone | 30 mg |
| Methyl p-hydroxybenzoate | 2 mg |
| Propyl p-Hydroxybenzoate | 0.3 mg |
| Purified Water | up to 1 g |
| A cylinder contains about 94% of solution and 6% of propellant (isobutane, n-butane, propane) | |
| (*): sodium diclofenac 4% | |

The description being thus described, these methods can obviously be modified in various ways. These modifications should not be considered as diverging from the spirit and perspectives of the invention and all the modifications which can appear evident to a skilled person in the field are included in the scope of the following claims.

The invention claimed is:

1. A method for the treatment of formed clots of fibrin and thrombi which are formed at the skin level by fibrinolysis/debridement of said clots and thrombi, said method comprising topically applying to a patient in need thereof a sulphated hyaluronic acid (HA), said sulphated hyaluronic acid being prepared starting from a hyaluronic acid (HA) having a molecular weight ranging from 10,000 to 50,000 Da, 150,000 to 250,000 Da or 500,000 to 750,000 Da and a sulphation degree equal to 1 or 3.

2. The method according to claim 1, wherein the sulphated hyaluronic acid is part of a pharmaceutical composition possibly associated with pharmacologically and/or biologically active agents.

3. The method according to claim 2, wherein the pharmaceutical composition comprises steroids, hormones, proteins, trophic factors, vitamins, non-steroid anti-inflammatory drugs, chemotherapy drugs for topical use, antibiotics, antiviral agents, local anesthetics, anticoagulants and/or fibrinolytic agents, enzymes and/or other proteases.

4. The method according to claim 3, wherein the pharmaceutical composition comprises hyaluronidase.

5. The method according to claim 4, wherein the pharmaceutical composition comprises polymers such as hyaluronic acid and its derivatives, carboxymethylcellulose and/or other polymers of a natural or synthetic origin.

6. The method according to any one of claims 2-5, wherein the pharmaceutical composition is in the form of an ointment, lipogel, hydrogel, lipstick, cream, patches, vaginal ovules and bougies, foam, mucosal gel, ophthalmic preparations, vaginal douches, mouthwash, solutions for topical application or inhalation.

7. The method according to claim 6, wherein the pharmaceutical composition comprises sulphated hyaluronic acid as skin absorption promoter of drugs in the form of an ointment, lipogel, hydrogel, lipstick, cream, patches, vaginal ovules and bougies, foam, mucosal gel, ophthalmic preparations, vaginal douches, mouthwash, solutions.

8. The method according to claim 7, wherein the pharmaceutical composition is in the form of patches containing sulphated hyaluronic acid in association with non-steroid anti-inflammatory drugs.

9. The method according to claim 8, wherein the pharmaceutical composition comprises diclofenac.

* * * * *